United States Patent
Esguerra Wilczynski et al.

(10) Patent No.: US 11,523,748 B2
(45) Date of Patent: Dec. 13, 2022

(54) CATHETER WITH SINGLE AXIAL SENSORS

(71) Applicant: BIOSENSE WEBSTER, INC., Irvine, CA (US)

(72) Inventors: Maribeth Esguerra Wilczynski, Glendale, CA (US); Jennifer Maffre, Pasadena, CA (US); Thanh Nguyen, El Monte, CA (US)

(73) Assignee: BIOSENSE WEBSTER, INC., Irvine, CA (US)

( * ) Notice: Subject to any disclaimer, the term of this patent is extended or adjusted under 35 U.S.C. 154(b) by 18 days.

(21) Appl. No.: 16/565,352

(22) Filed: Sep. 9, 2019

(65) Prior Publication Data
US 2020/0015703 A1    Jan. 16, 2020

Related U.S. Application Data

(63) Continuation of application No. 14/445,021, filed on Jul. 28, 2014, now Pat. No. 10,405,774, which is a (Continued)

(51) Int. Cl.
*A61B 5/06* (2006.01)
*A61B 34/20* (2016.01)
(Continued)

(52) U.S. Cl.
CPC .............. *A61B 5/062* (2013.01); *A61B 5/341* (2021.01); *A61B 34/20* (2016.02); *A61M 25/005* (2013.01);
(Continued)

(58) Field of Classification Search
None
See application file for complete search history.

(56) References Cited

U.S. PATENT DOCUMENTS 4,815,478 A    3/1989 Buchbinder et al.
RE34,502 E     1/1994 Webster, Jr.
(Continued)

FOREIGN PATENT DOCUMENTS

CN    101675879 A    3/2010
CN    101708130 A    5/2010
(Continued)

OTHER PUBLICATIONS

Extended European Search Report dated Feb. 14, 2012 for EP 11191759.7, 3 pages.
(Continued)

*Primary Examiner* — Shahdeep Mohammed
(74) *Attorney, Agent, or Firm* — Lewis Roca Rothgerber Christie LLP

(57) ABSTRACT

A catheter has single axis sensors mounted directly along a portion of the catheter whose position/location is of interest. The magnetic based, single axis sensors are on a linear or nonlinear single axis sensor (SAS) assembly. The catheter includes a catheter body and a distal 2D or 3D configuration provided by a support member on which at least one, if not at least three single axis sensors, are mounted serially along a length of the support member. The magnetic-based sensor assembly may include at least one coil member wrapped on the support member, wherein the coil member is connected via a joint region to a respective cable member adapted to transmit a signal providing location information from the coil member to a mapping and localization system. The joint region provides strain relief adaptations to the at least one coil member and the respective cable member from detaching.

19 Claims, 32 Drawing Sheets

Related U.S. Application Data continuation of application No. 12/982,765, filed on Dec. 30, 2010, now Pat. No. 8,792,962.

(51) Int. Cl.
| | |
|---|---|
| *A61M 25/00* | (2006.01) |
| *A61M 25/01* | (2006.01) |
| *A61B 17/00* | (2006.01) |
| *A61B 5/341* | (2021.01) |

(52) U.S. Cl.
CPC ... *A61M 25/0136* (2013.01); *A61B 2017/003* (2013.01); *A61B 2017/00044* (2013.01); *A61B 2017/00053* (2013.01); *A61B 2017/00323* (2013.01); *A61B 2017/00845* (2013.01); *A61B 2034/2051* (2016.02); *A61B 2562/17* (2017.08)

(56) References Cited

U.S. PATENT DOCUMENTS

| | | | |
|---|---|---|---|
| 5,275,151 A | | 1/1994 | Shockey et al. |
| 5,391,199 A | | 2/1995 | Ben-Haim |
| 5,395,329 A | | 3/1995 | Fleischhacker et al. |
| 5,443,489 A | | 8/1995 | Ben-Haim |
| 5,645,065 A | | 7/1997 | Shapiro et al. |
| 5,656,029 A | | 8/1997 | Imran et al. |
| 5,891,088 A | | 4/1999 | Thompson et al. |
| 5,997,473 A | * | 12/1999 | Taniguchi ............... A61B 5/062 600/117 |
| 6,123,699 A | | 9/2000 | Webster, Jr. |
| 6,171,277 B1 | | 1/2001 | Ponzi |
| 6,183,463 B1 | | 2/2001 | Webster, Jr. |
| 6,484,118 B1 | | 11/2002 | Govari |
| 6,491,681 B1 | | 12/2002 | Kunis et al. |
| 6,500,129 B1 | | 12/2002 | Mahurkar |
| 6,554,794 B1 | | 4/2003 | Mueller et al. |
| 6,574,492 B1 | | 6/2003 | Ben-Haim et al. |
| 6,690,963 B2 | | 2/2004 | Ben-Haim et al. |
| 6,788,967 B2 | | 9/2004 | Ben-Haim et al. |
| 6,892,090 B2 | | 5/2005 | Verard |
| 6,961,602 B2 | | 11/2005 | Fuimaono et al. |
| 7,174,202 B2 | | 2/2007 | Bladen et al. |
| 7,274,957 B2 | | 9/2007 | Drysen |
| 7,615,044 B2 | | 11/2009 | Scheibe et al. |
| 7,931,616 B2 | | 4/2011 | Selkee |
| 8,118,775 B2 | | 2/2012 | Grunewald et al. |
| 8,382,662 B2 | | 2/2013 | Soper et al. |
| 8,529,505 B2 | | 9/2013 | Grunewald et al. |
| 8,700,133 B2 | | 4/2014 | Hann |
| 8,792,962 B2 | | 7/2014 | Esguerra et al. |
| 8,805,472 B2 | | 8/2014 | Iglesias |
| 8,880,147 B2 | | 11/2014 | Tegg et al. |
| 8,926,528 B2 | | 1/2015 | Govari et al. |
| 8,936,583 B2 | | 1/2015 | Holzbauer et al. |
| 2003/0028096 A1 | | 2/2003 | Niwa et al. |
| 2003/0160721 A1 | | 8/2003 | Gilboa et al. |
| 2005/0274425 A1 | | 12/2005 | Ostrander et al. |
| 2007/0164900 A1 | * | 7/2007 | Schneider ............... A61B 34/20 342/357.75 |
| 2008/0255540 A1 | | 10/2008 | Selkee |
| 2009/0005754 A1 | | 1/2009 | Soetermans |
| 2009/0192412 A1 | * | 7/2009 | Sela ................ A61B 17/00234 600/585 |
| 2010/0036285 A1 | | 2/2010 | Govari |
| 2010/0069834 A1 | | 3/2010 | Schultz |
| 2010/0168827 A1 | | 7/2010 | Schultz |
| 2010/0222664 A1 | * | 9/2010 | Lemon .................. A61B 5/283 600/409 |
| 2011/0054287 A1 | | 3/2011 | Schultz |
| 2012/0143088 A1 | | 6/2012 | Schultz |
| 2012/0172842 A1 | | 7/2012 | Sela et al. |
| 2014/0228838 A1 | | 8/2014 | Kirschenman |
| 2014/0275957 A1 | | 9/2014 | Lupotti |

FOREIGN PATENT DOCUMENTS

| | | |
|---|---|---|
| CN | 101925333 A | 12/2010 |
| EP | 1457226 B1 | 4/2007 |
| EP | 1562665 B1 | 5/2010 |
| EP | 2151209 A3 | 1/2011 |
| EP | 2165730 B1 | 6/2011 |
| EP | 2460558 A1 | 6/2012 |
| EP | 2 471 455 A2 | 7/2012 |
| EP | 2301617 B1 | 10/2012 |
| EP | 2897524 B1 | 9/2016 |
| JP | 2010-36040 A | 2/2010 |
| WO | WO9634652 A1 | 11/1996 |
| WO | WO2007130720 A1 | 11/2007 |

OTHER PUBLICATIONS

Partial European Search Report dated Jun. 25, 2012 for EP 11196031, 6 pages.
Extended European Search Report dated Sep. 17, 2012 for EP 11196031, 12 pages.
European Patent Office Search Report dated May 26, 2017 for EP Application No. 16206180.8, 9 pages.
Notification of Reasons for Refusal (English Translation Only) for Japanese Patent Application No. 2011-288664, dated Nov. 24, 2015, 5 pages.
Australian Examination Report for Patent Application No. 2011265578, dated Jun. 3, 2014, 5 pages.
Canadian Office action for Patent Application No. 2,762,297, dated Oct. 18, 2017, 4 pages.
English translation of first Office Action for Patent Application No. CN 201110462725.9, dated Dec. 25, 2014, 4 pages.
EPO Communication for Application No. 11 196 031.6, dated Sep. 26, 2013, 4 pages.
Australian Examination Report No. 1 for Application No. 2015203371, dated Mar. 16, 2016, 4 pages.

* cited by examiner

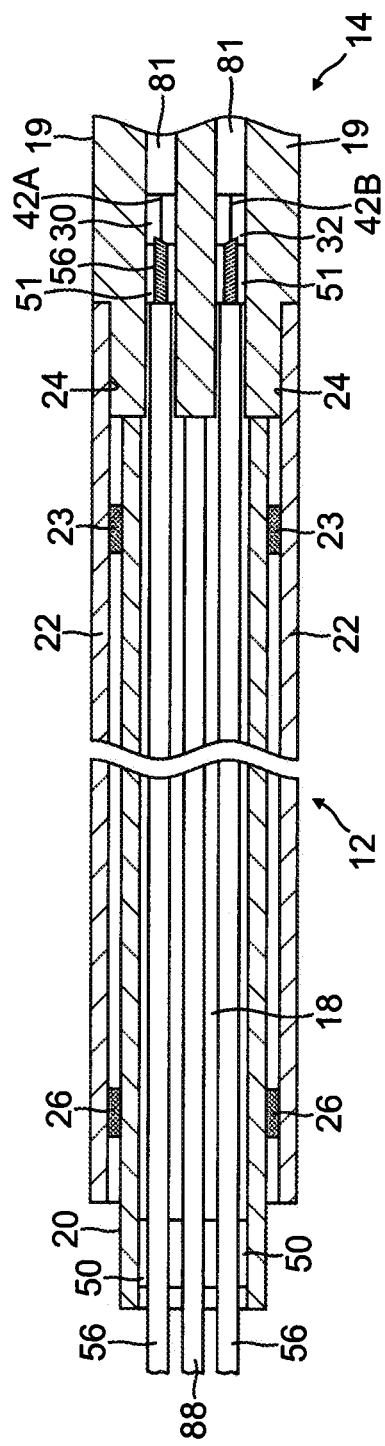

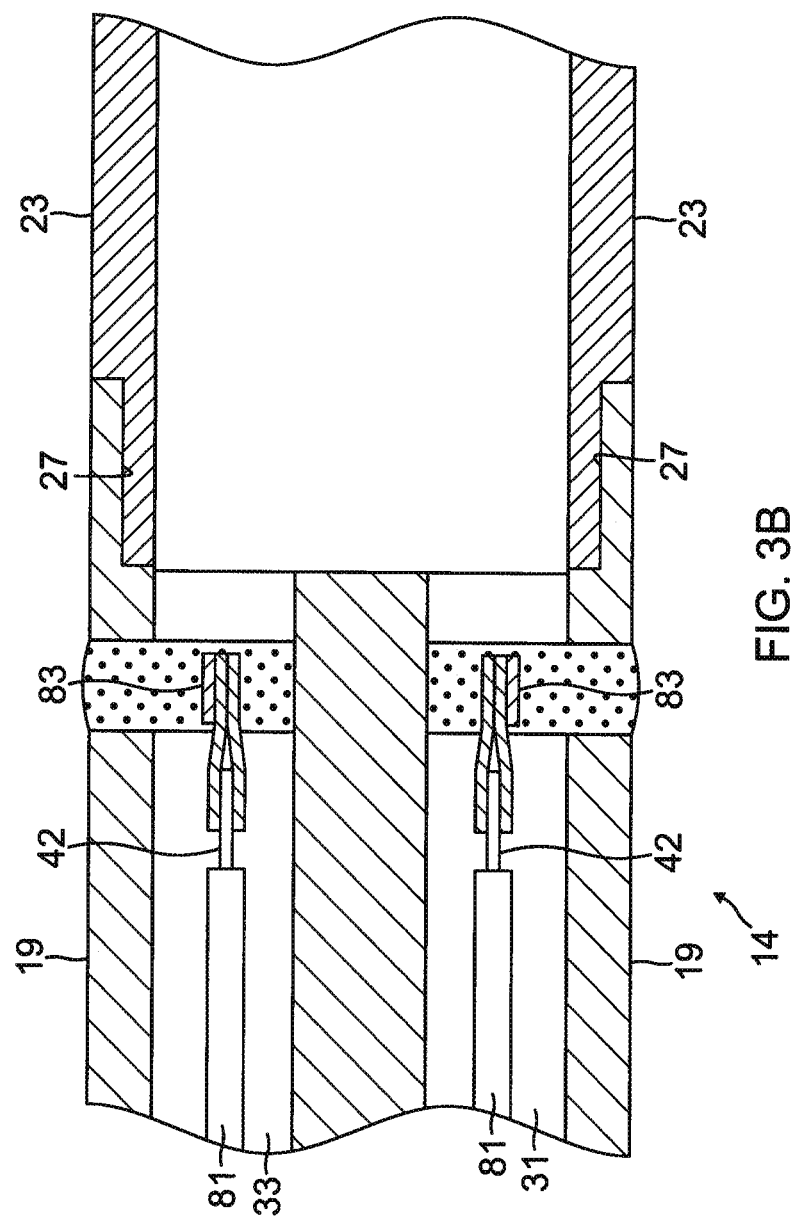

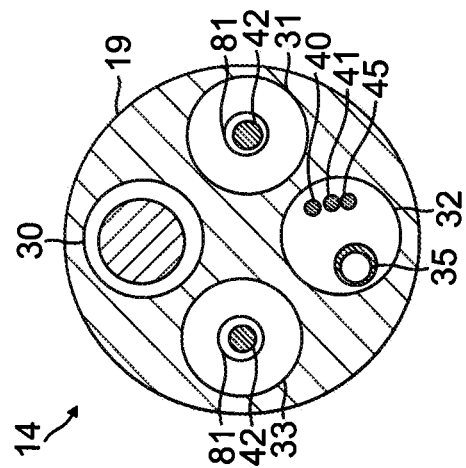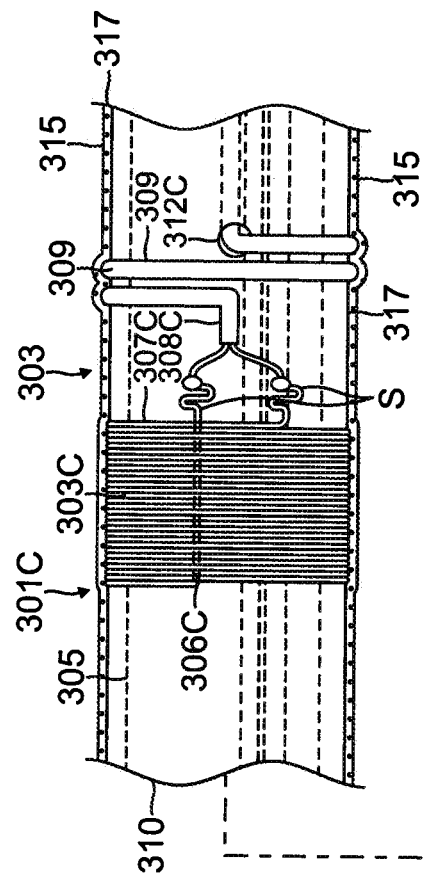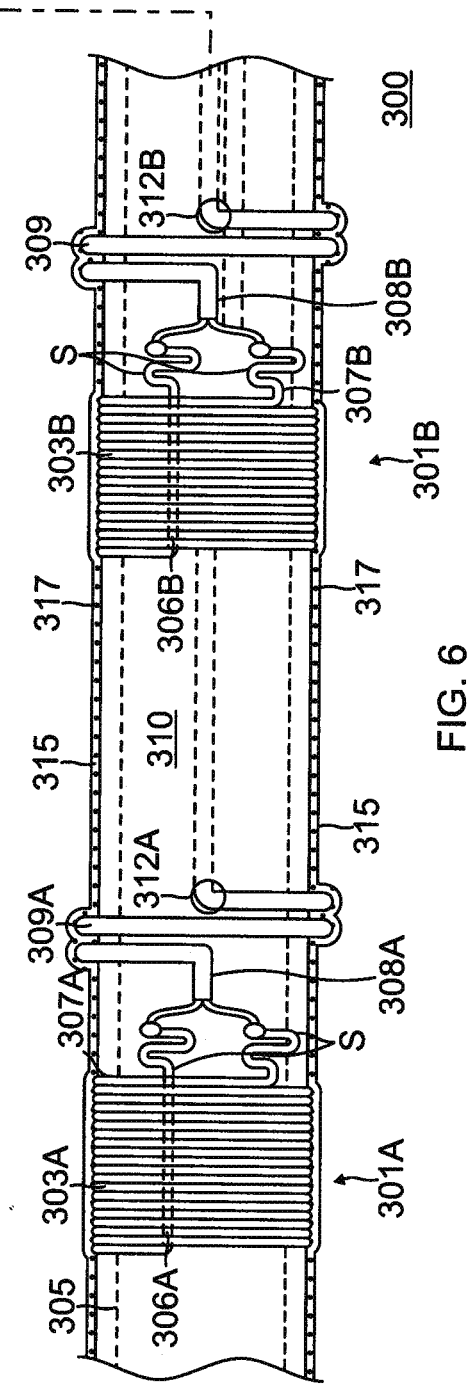

CATHETER WITH SINGLE AXIAL SENSORS

CROSS REFERENCE TO RELATED APPLICATIONS

This application is a continuation of and claims priority to and the benefit of U.S. application Ser. No. 14/445,021 filed Jul. 28, 2014, now U.S. Pat. No. 10,405,774, which is a continuation of and claims priority to and the benefit of U.S. application Ser. No. 12/982,765 filed Dec. 30, 2010, now U.S. Pat. No. 8,792,962, the entire contents of all of which are incorporated herein by reference.

FIELD OF INVENTION

This invention relates to a catheter, in particular, a catheter having location sensors mounted on flexible distal end portion for improved position sensing of the distal end portion.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Viewing of the catheter distal tip during a mapping and/or ablation procedure is a major benefit. In particular, being able to see a shaft of the catheter in relation to the distal tip would allow the operating physician to understand catheter orientation in relation to the other catheters found in the same region or chamber of the heart. U.S. Pat. Nos. 5,391, 199, 5,443,489, 6,788,967 and 6,690,963 to Ben-Haim, whose entire disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally applied magnetic fields. The magnetic fields are generated by three radiator coils, fixed to an external reference frame in known, mutually spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

It is known to provide the three radiator coils in a biosensor that is carried in a distal tip section of a catheter. Where the catheter has a distal tip with a 2-dimensional or 3-dimensional flexible configuration with shape-memory, the biosensor is typically carried proximally of the configuration for a number of reasons, including the fragile nature of the biosensor and the lack of space in the configuration. However, because the biosensor is not carried on the configuration, a certain amount of human guesswork and/or proximation by the mapping and localization system is applied to determine the location and position of the configuration.

Accordingly, a desire exists for a catheter that can provide more accurate signals of the location of its distal end, especially where the distal end includes a 2- or 3-dimensional configuration with shape-memory.

SUMMARY OF THE INVENTION

The present invention is directed to a catheter with improved position and/or location sensing with the use of single axis sensors that are mounted directly on a length or portion of the catheter whose position/location is of interest. The magnetic based, single axis sensors are provided on a single axis sensor (SAS) assembly, which can be linear or nonlinear as needed. A catheter of the present invention thus includes a catheter body and a distal member of a particular 2D or 3D configuration that is provided by a support member on which at least one, if not at least three single axis sensors are mounted serially along the length of the support member.

In one embodiment, the magnetic-based sensor assembly including at least one coil member that is wrapped on the support member, wherein the coil member is connected via a joint region to a respective cable member adapted to transmit a signal providing location information from the coil member to a mapping and localization system. The joint region advantageously provides strain relief adaptations to the at least one coil member and the respective cable member from detaching. In a more detailed embodiment, the support member can be tubing, such as polyimide tubing, or a shape-memory member, such as a nitinol member. Also, a protective tubing is provided over the assembly to encapsulate the single axis sensor. Space under the tubing is filled with epoxy or other suitable materials to fix the components under the tubing. Endcaps at each end of the tubing may also be formed with epoxy or other suitable materials.

Where the SAS assembly is linear, it is suitable for use in a lumen of an intermediate deflection section of the catheter for improved mapping and location sensing of the generally linear structure of the intermediate deflection section. Where the SAS assembly is nonlinear, it is suitable for use in a "lasso" assembly for improved mapping and location sensing of the generally non-linear structure of the lasso assembly.

Where the SAS assembly includes multiple single axis sensor arranged serially a predetermine distance from each other along the support member, a nonconductive tubing is provided under the coil sensor of the more proximal sensor(s) so that cable(s)s from the more distal sensor(s) can extend under the tubing for isolation from the coil sensor.

In a more detailed embodiment, strain relief adaptations include providing a predetermine amount of slack in coil wire in the joint region and winding of the cable around the support member to better anchor the joint region against damage and detachment. Cables from each sensor are wound more loosely along the length of the support member, the plurality of cables increasing with the windings passing each sensor toward the proximal end of the support member. A heat shrink tubing is provided along generally the entire length of the support member, over each sensor, to protect, isolate and seal the sensors.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2A is a side cross-sectional view of an embodiment of a junction of a catheter body and an intermediate section, taken along a first diameter.

FIG. 3B is a side cross-sectional view of the junction of FIG. 3A, taken along a second diameter generally perpendicular to the first diameter.

FIG. 4 is a longitudinal cross-sectional view of the intermediate section of FIG. 3A, taken along line 4-4.

FIG. 6 is a side view of an embodiment of a linear single axis sensor assembly in accordance with the present invention.

DETAILED DESCRIPTION OF THE INVENTION

Figure 1:
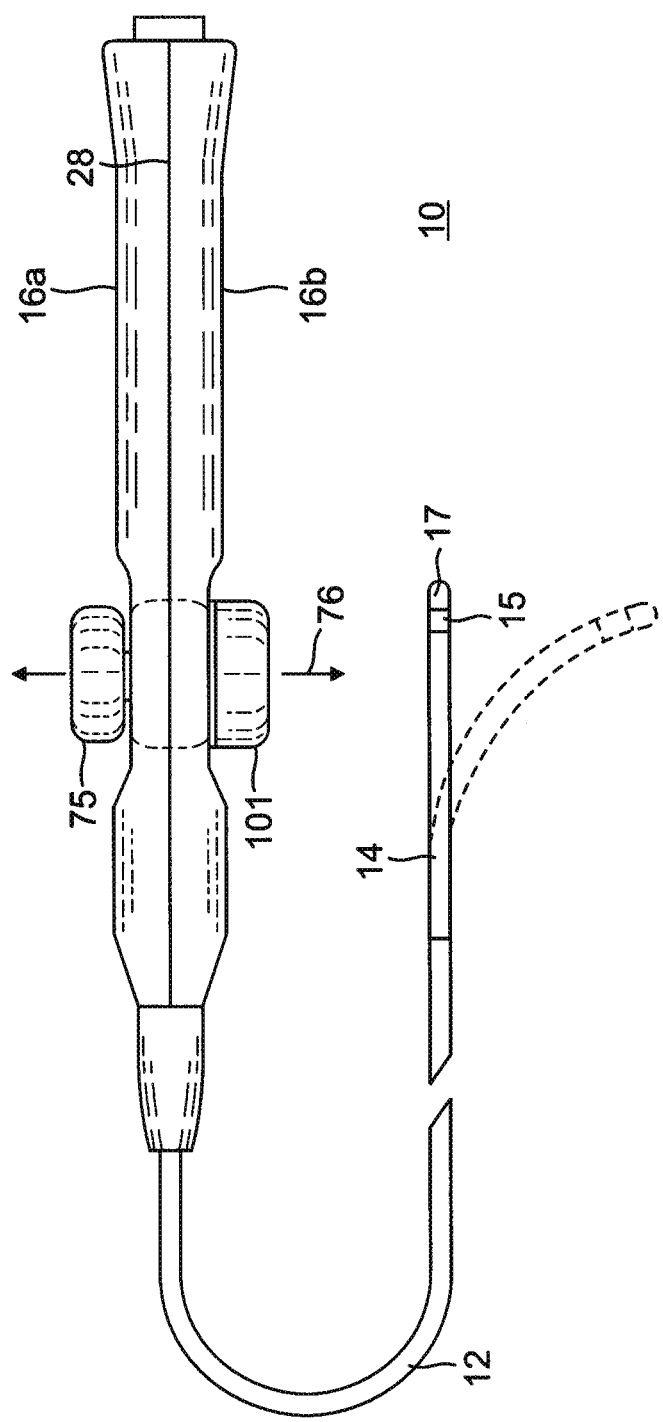
FIG. 1 is a top plan view of one embodiment of the catheter of the present invention.

Referring to FIG. 1, the present invention is directed to a catheter 10 with at least one single axis sensor, if not three or more single axis sensors, mounted on a distal end section 15 that is distal of at least a catheter body 12 if not also an intermediate deflectable section 14. In the illustrated embodiment, the distal end section 15 includes a tip electrode 17. At the proximal end of the catheter body 12 is a multi-functional control handle 16 with mechanisms that are manipulated by a user to accomplish, for example, bi-directional deflection of the intermediate section 14.

Figure 2B:
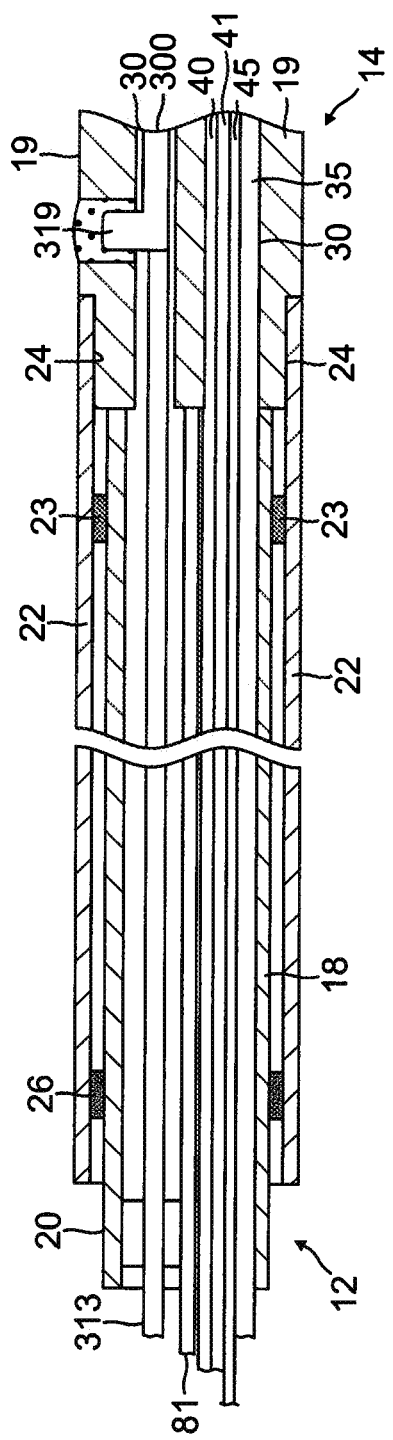
FIG. 2B is a side cross-sectional view of the junction of FIG. 2a, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. A suitable construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner. A single lumen catheter body 12 can be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, e.g., polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter a second glue joint 26 is formed between the proximal ends of the stiffening tube 20 and outer wall 22 using a slower drying but stronger glue, e.g., polyurethane.

The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

As shown in FIGS. 2A, 2B and 4, the intermediate section 14 comprises a shorter section of tubing 19 with multiple off-axis lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2A and 2B, extending through the single lumen 18 of the catheter body 12 are various components, for example, lead wires and multiple puller members, and any other wires or cables. Longitudinal movement of the puller members relative to the catheter body 12 enable user control of various parts of the catheter via the control handle. In one embodiment, the puller members include a pair of deflection puller members 42 for bi-directionally deflecting the intermediate section 14.

A deflection puller member 42 extends through the central lumen 18 of the catheter body 12 and into the second lumen 31 of the intermediate section 14. Another deflection puller member 42 extends through the central lumen 18 and into the fourth lumen 33 of the intermediate section 14. The distal ends of the deflection puller members 42 are anchored to the wall of the tubing 19 near the distal end of the intermediate section 14 by means of T-anchors 83 (FIG. 3B). In the intermediate section 14, each deflection puller members 42 extends through a plastic, e.g., Teflon®, sheath 81, which prevents the deflection puller members 42 from cutting into the wall of the tubing 19 of the intermediate section 14 when the intermediate section 14 is deflected.

As shown in FIG. 2A, compression coils 56 in surrounding relation to the deflection puller members 42 extend from the proximal end of the catheter body 12 to the proximal end of the intermediate section 14. The compression coils 56 are made of any suitable metal, e.g., stainless steel. The compression coils 56 are tightly wound on itself to provide flexibility, i.e., bending, but to resist compression. The inner diameter of the compression coils 56 is preferably slightly larger than the diameter of the puller wires 42. For example, when a puller member 42 has a diameter of about 0.007 inches, the compression coil 56 preferably has an inner diameter of about 0.008 inches. The Teflon®. coating on the puller member 42 allows them to slide freely within the compression coils. The outer surface of the compression coils can be covered by a flexible, non-conductive sheath to prevent contact between the compression coils and other components, such as lead wires and cables, etc. A nonconductive sheath can be made of polyimide tubing.

The compression coils 56 are anchored at their proximal ends to the proximal end of the stiffening tube 20 in the catheter body 12 by glue joint 50 (FIG. 2B) and at its distal end near the proximal end of the intermediate section 14 in the second lumen 31 and fourth lumen 33 by glue joints 51 (FIG. 2B).

Figure 3A:
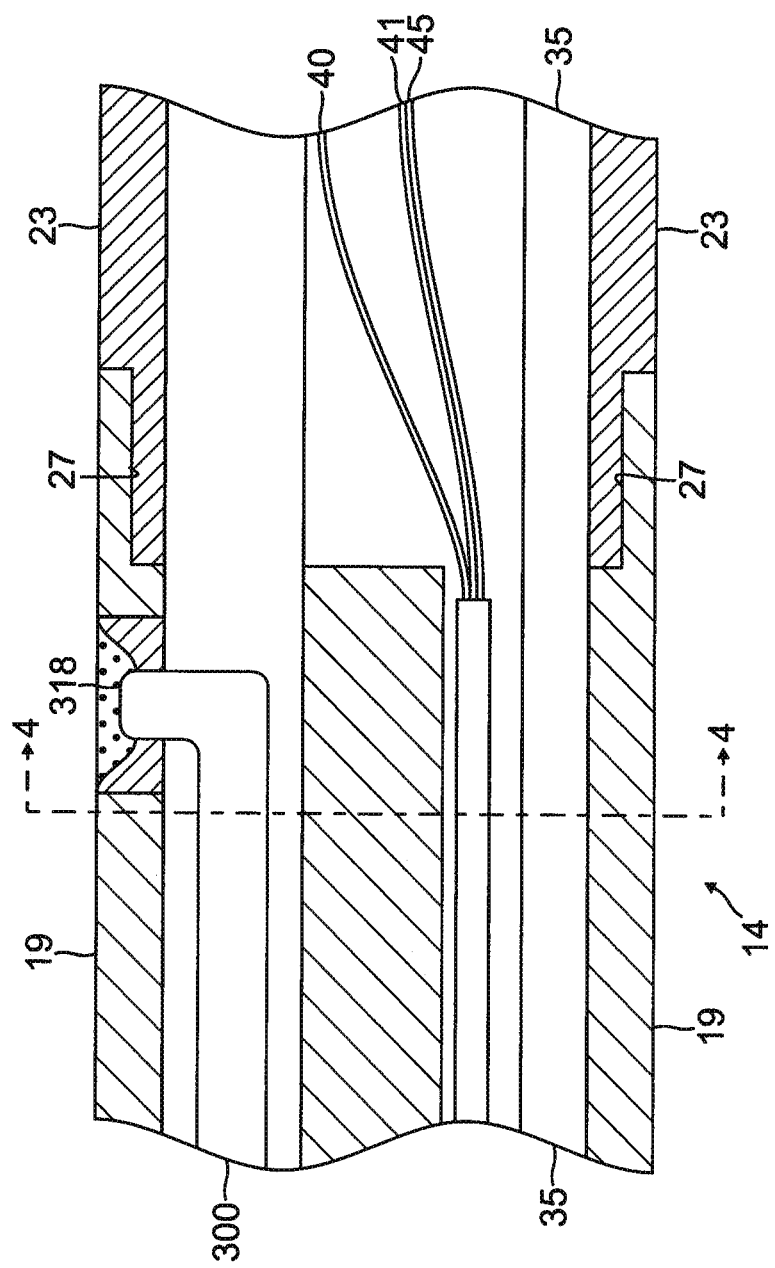
FIG. 3A is a side cross-sectional view of the embodiment of a junction of the intermediate section and a distal tip section, along a first diameter.
Figure 5:
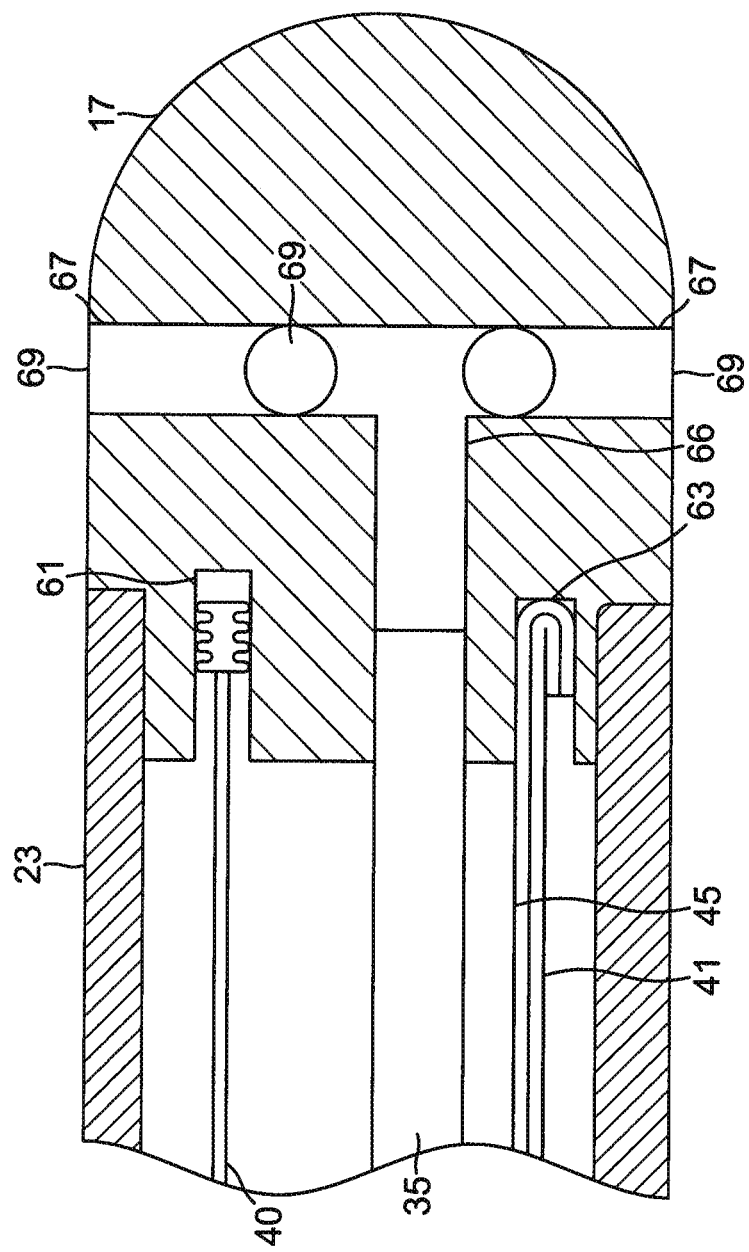
FIG. 5 is a side cross-sectional view of an embodiment of a distal tip section of the catheter of the present invention.

As illustrated in FIGS. 3A, 3B and 5, the tip section 15 includes the tip electrode 17 which may be connected to the tubing 22 of the intermediate section 14 by means of a single lumen connector tubing 23. The connector tubing provides transition space for the various components extending from the tubing 22 to reorient themselves as needed for anchoring in the tip electrode 17. To that end, a distal surface of the tip electrode is provided with blind holes. In the disclosed embodiment, blind hole 61 is provided to receive a distal end of the tip electrode lead wire 40, blind hole 63 to receive a distal end of the thermocouple wires 43 and 44. Irrigation passage 66 is also formed in the tip electrode to receive a distal end of the irrigation tubing 35. The passage 66 is in communication with transverse branches 67 and fluid ports 69 allowing fluid delivered through the tubing 35 to pass to outside of the tip electrode.

In accordance with a feature of the present invention, first lumen 30 of the intermediate deflection section 14 carries a linear single axis sensor ("SAS") assembly 300, a detailed embodiment of which is shown in FIG. 6. The SAS assembly carries at least one, if not three single axis sensors 301, for sensing location and/or position of a length of the intermediate deflection section 14. The sensors enable any portion of the catheter carrying the SAS assembly to be viewed under mapping systems manufactured and sold by Biosense Webster, Inc., including the CARTO, CARTO XP and NOGA mapping systems.

The linear SAS assembly 300 includes a generally linear support member of a predetermined length, for example, a relative stiff, triple walled polyimide tubing 305 of a predetermined length with a durometer ranging between about 80 and about 83, and more preferably between about 81 and about 82. The tubing has a single lumen 310 and carries the single axis sensors 301 serially along its length. Where there are three single axis sensors, the assembly carries a distal sensor 301A, a mid sensor 301B and a proximal sensor 301C. Each sensor includes a conducting member 303, e.g., a very fine small gauge wire, that is wound repeatedly around the tubing 305 to form a sensing coil as understood by one of ordinary skill in the art. A distal portion 306 of the wire extends proximally under the coil. The distal portion 306 and a proximal portion 307 of the wire both extend proximally past the coil and are each joined, e.g., by soldering, to a respective exposed distal end of a wire encased in a dual side-by-side wire cable 308 at a joint region located just proximal of the coil 303. Each joint region includes a strain relief adaption. The adaptation includes each end of the wire being provided with a predetermined amount of slack S distal of the soldering so as to minimize the risk of breakage and detachment in the joint region. Moreover, the cable 308 also provides strain relief for the sensor against breakage. In the disclosed embodiment, the strain relief includes multiple windings 309 of the cable, for example, about 720 degrees, generally transversely, around the tubing to anchor the soldered joints between the coil wire 303 and the cable 308. Proximal of the strain relief adaption, the cable 308 enters the central lumen 310 of the tubing 305 via an aperture 312 form in the wall of the tubing 305, where it extends proximally toward the control handle and beyond toward the mapping and localization system for processing signals sensed by the sensors 301A, 301B, 301C. The assembly allows for the sensor to retain its shape while protecting the connection to each sensor. The tubing 305 physically and electrically isolates the wire and cable from other components in the catheter. The tubing also protects and shields the wire and cable from damage during construction and use of the catheter. It also functions as a scaffold to the sensor to retain its shape.

As mentioned, the disclosed embodiment provides three single axis sensors, each of has a similar structure as described above. Proximal the proximal sensor, cables 308 extend proximally in parallel through the central lumen 310 toward the control handle and beyond toward the mapping and localization system. To protect the fragile and delicate nature of the single axis sensors and the soldered joints with the cables, a heat shrink sleeve 315 (shown in a side cross-sectional view in FIG. 6) is included with assembly 300 covering each of the coils, the soldered joints and the strain relief adaptations. Epoxy, UV glue and/or similar material 317 (also shown in a side cross-sectional view in FIG. 6) is injected into the heat shrink sleeve 317 to provide further support to the SAS assembly 300 by potting and fixing the coils and the strain relief adaptations onto the tubing and in the heat shrink sleeve. The epoxy provides an added degree of rigidity to the SAS assembly 300 as further protection against breakage and detachment of the coil wires and the sensor cables but does not adversely affect deflection of the intermediate section 14.

Each single axis sensor 301 of the linear SAS assembly 300 thus includes a respective coil 301, a respective dual-wire cable 308, respective strain relief adaptations including the wire slack S and the cable windings 309, and respective solder joints electronically coupling the coil and the cable. With reference to the embodiments of FIGS. 2B and 3A, distal and proximal ends 318, 319 of the support member 305 are anchored at or near the distal and proximal end of the tubing 19 of the intermediate deflectable section 14. The cables 308A, 308B, 308C extend proximally from the assembly 300 through the lumen 30 of the tubing of the intermediate section 14 and the central lumen 18 of the catheter body toward the mapping and localization system. A protective, nonconductive sheath 313 can be provided for the cables.

In manufacturing the linear SAS assembly 300, the distal sensor coil 303A is wound on the tubing 305, followed by soldering of the ends 306A, 307A to the spliced distal end of cable 308A which is then fed into the central lumen 310 via the aperture 312A formed by perforation with a preheated needle or in any similar method. At predetermined distance proximal of the distal sensor coil 303A, the mid-sensor coil 303B is wound on the tubing 305 followed by soldering of ends 306B, 306B to spliced distal end of cable which 308B is then fed into the central lumen 310 via the aperture 312B to extend along with the cable 308A toward the mapping and localization system. At a predetermined distance proximal of the mid sensor coil 303B, the proximal coil 303C is wound on the tubing 305 followed by soldering of ends 306C, 307C to spliced distal end of cable 308C which is fed into the central lumen 310 via aperture 312C to extend along with the cables 308A, 308B toward the mapping and localization system. The heat shrink sleeve 315 is placed over the tubing and all the components to protect and seal the assembly 300. Epoxy 317 is then injected into as a filler into the space between the sleeve and the components. The assembly 300 is then inserted into the lumen 30 of the tubing 19 of the intermediate section 14 (or any other suitable portion of the catheter) with the cables 308A, 308B, 308C extending through the lumen 30 of the intermediate section 14 and then central lumen 18 of the catheter body 12. The assembly 300 is sufficiently flexible to allow deflection of the intermediate section 14 as needed or appropriate.

Figure 7:
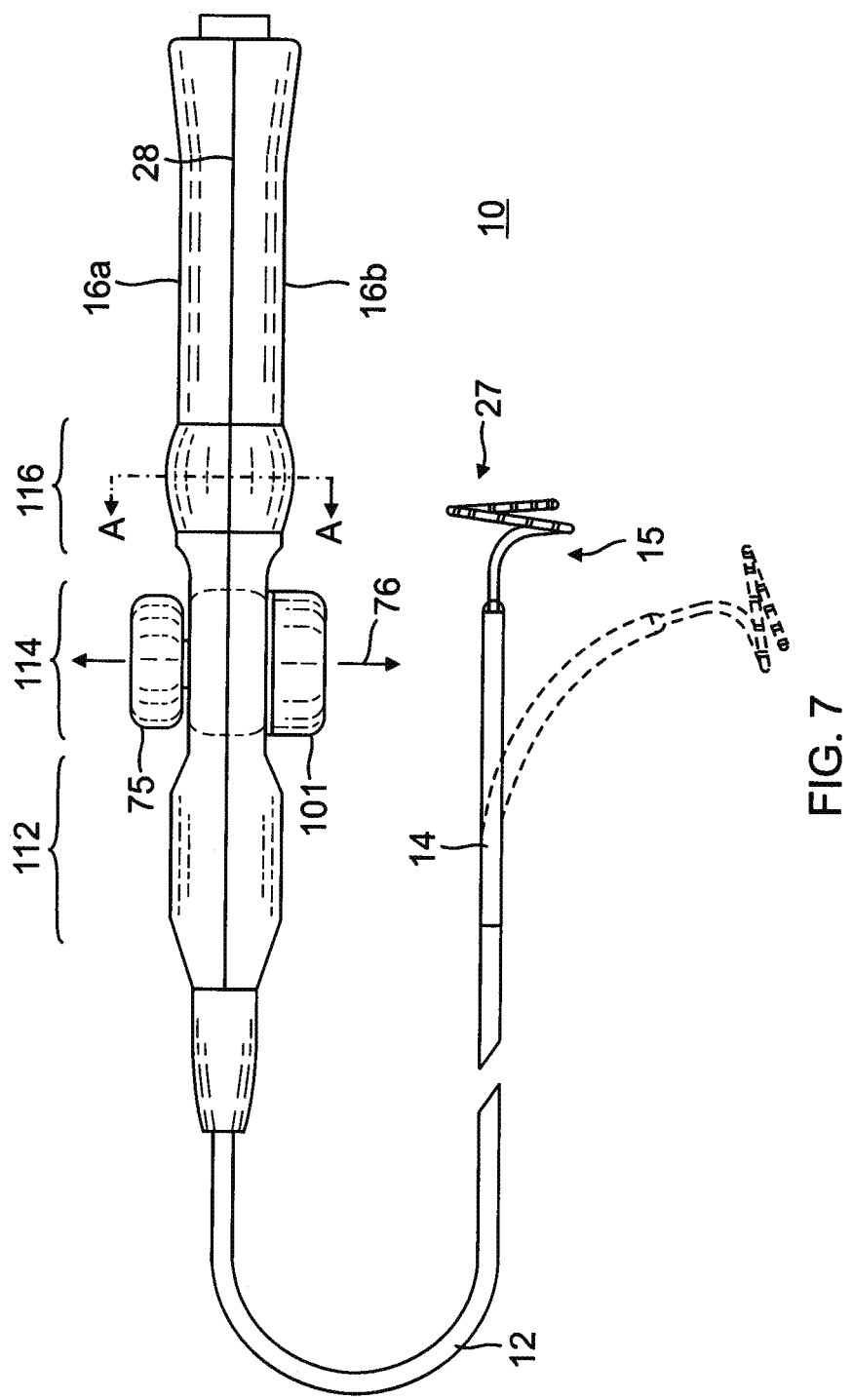
FIG. 7 is a top plan view of another embodiment of the catheter of the present invention.

In an alternate embodiment as shown in FIG. 7, the distal section 15 distal of the intermediate shaft 14 is 3-D configuration, for example, a mapping assembly 27.

Figure 8A:
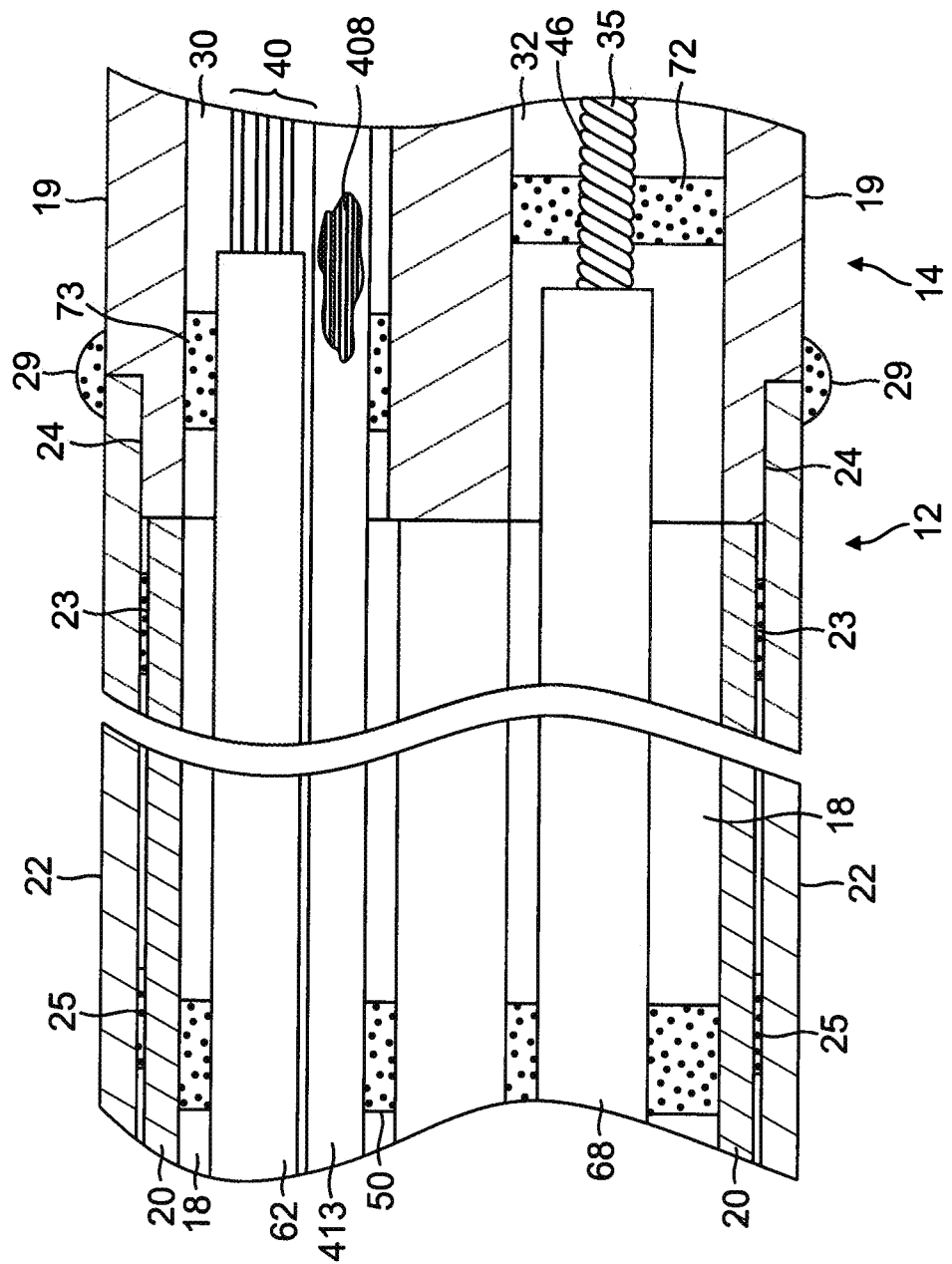
FIG. 8A is a side cross-sectional view of an embodiment of a junction of a catheter body and an intermediate section, taken along a first diameter.
Figure 8B:
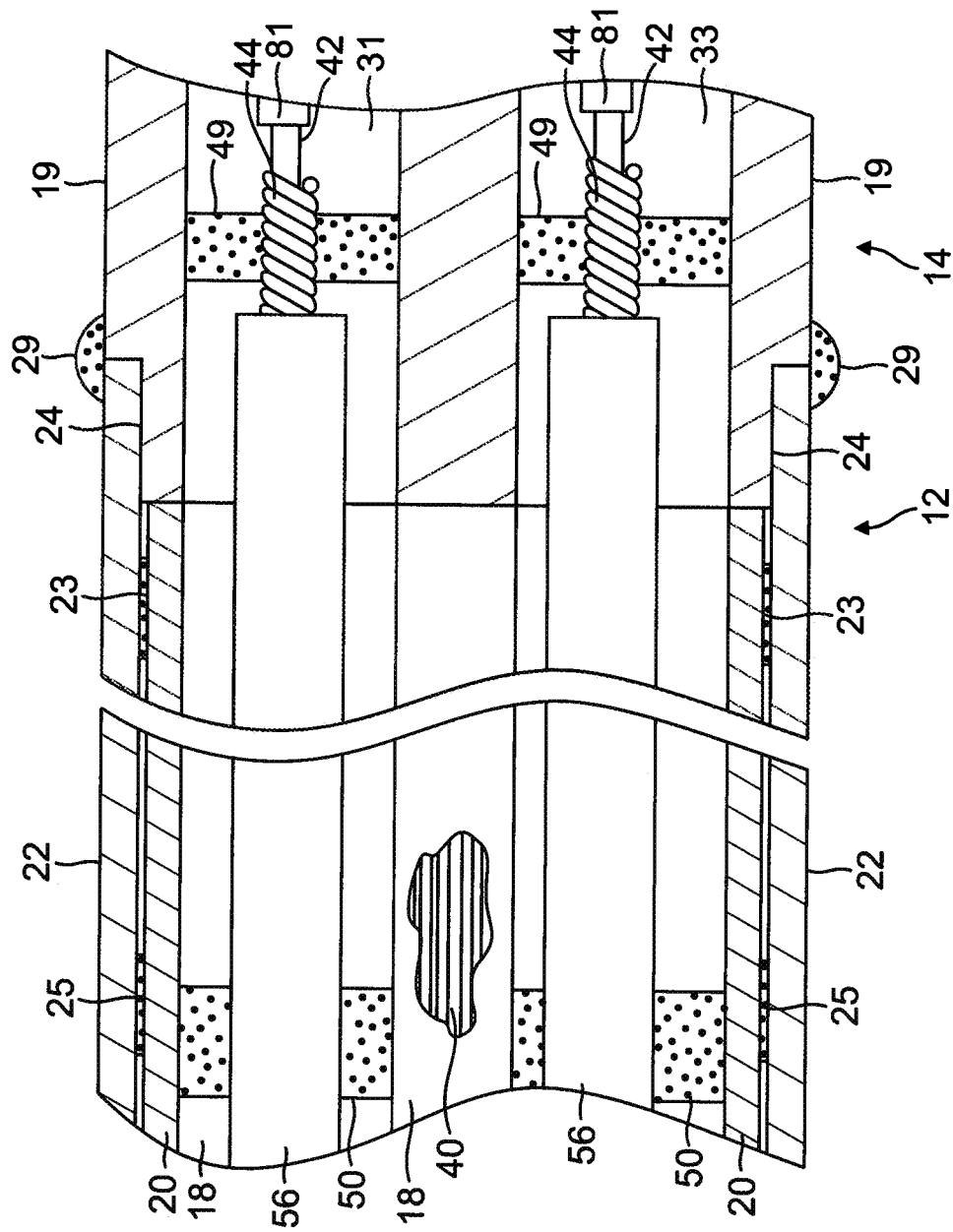
FIG. 8B is a side cross-sectional view of the junction of FIG. 8A, taken along a second diameter generally perpendicular to the first diameter.
Figure 10:
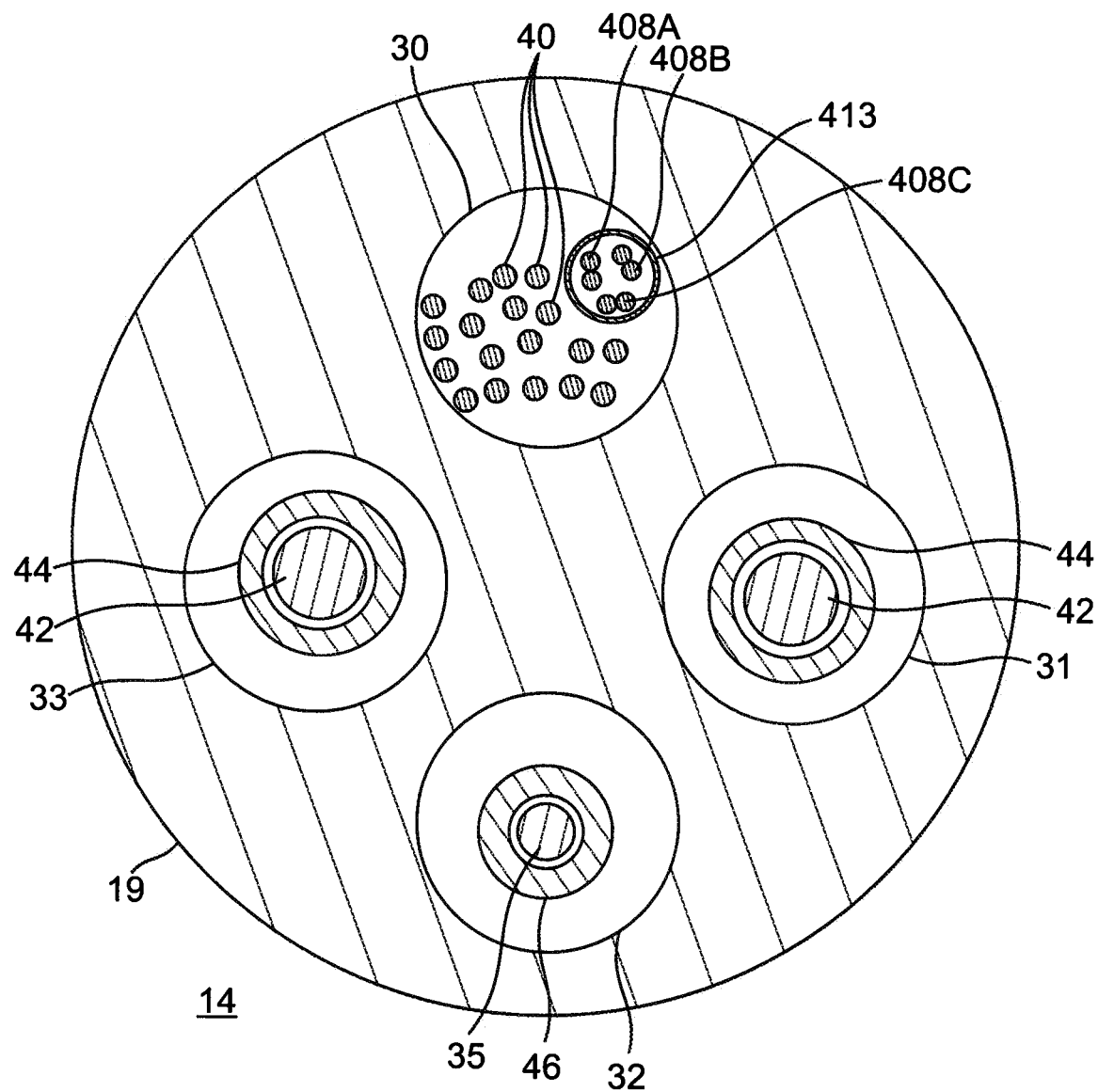
FIG. 10 is a longitudinal cross-sectional view of the intermediate section of FIG. 9, taken along line 10-10.

A disclosed embodiment of the catheter body 12 and the intermediate deflection section 14 are illustrated in FIGS. 8A, 8B and 10. Construction and structure are similar to the above-described embodiment and thus the above description similarly applies. However, differences include adaptations for accommodating the mapping assembly 17, as illustrated and understood by one of ordinary skill in the art.

Figure 9:
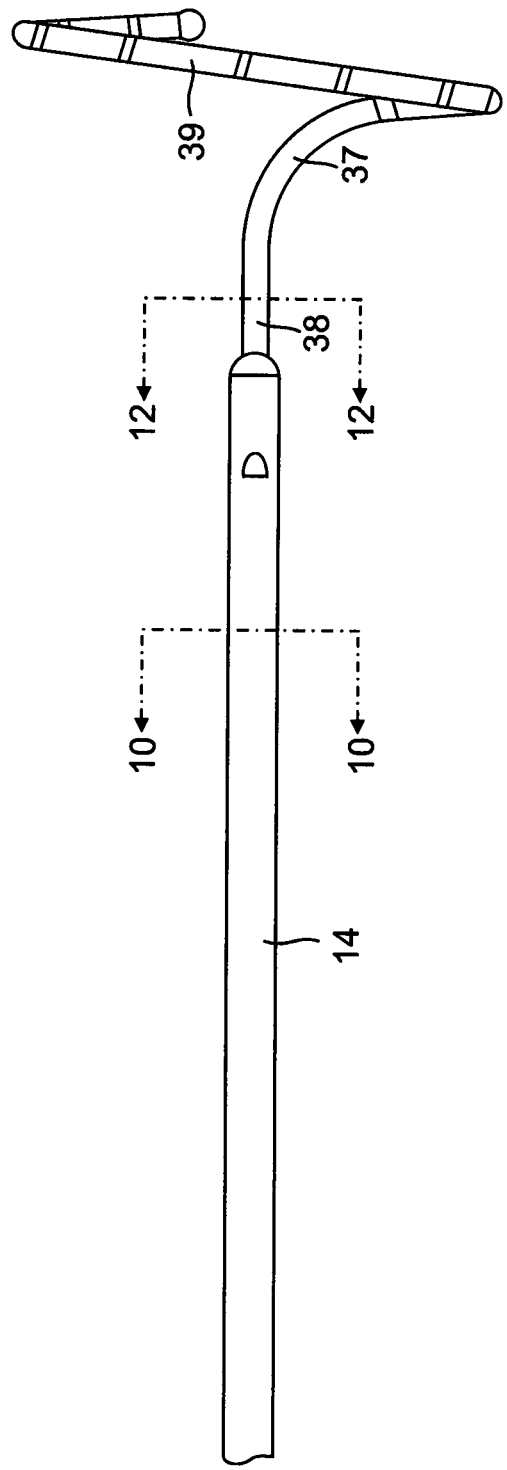
FIG. 9 is a side view of a distal portion of the catheter of FIG. 7, including an intermediate section and a mapping assembly.

With reference to FIG. 9, the mapping assembly 27 comprises a generally straight proximal region 38 and a generally circular main region 39. The proximal region 38 is mounted on the intermediate section 14, as described in more detail below, so that it is generally a linear extension of the intermediate section 14. In one embodiment, the proximal region 38 has an exposed length, e.g., not contained within the intermediate section 14, ranging from about 3 mm to about 12 mm, more preferably about 3 mm to about 8 mm, still more preferably about 5 mm, but can vary as desired. An "elbow" 37 is formed between the proximal region 38 and the generally circular main region to accommodate the angular transition therebetween.

The generally circular main region 39 is generally traverse, if not also perpendicular, to the catheter body 12. The generally circular main region 39 can form a flat circle or can be very slightly helical. In one embodiment, the main region 39 has an outer diameter ranging from about 10 mm to about 25 mm, more preferably about 12 mm to about 20 mm. The generally circular main region 39 can curve in a clockwise direction or a counterclockwise direction. As shown in FIGS. 11, 12, 13, 14A and 14B, the mapping assembly 17 is formed of a non-conductive cover or tubing 52 which can have any cross-sectional shape as desired. The non-conductive cover 52 can be made of any suitable material, and is preferably made of a biocompatible plastic such as polyurethane or PEBAX. The non-conductive cover 52 can be pre-formed into the desired generally circular shape of the generally circular main region 39. Alternatively, the shape of the generally circular main region 39 can be defined by a wire or other component extending through the non-conductive cover 52.

In the depicted embodiment, a pre-formed support member 54 extends through the non-conductive cover 52 to define the shape of the generally circular main region 39. The support member 54 is made of a material having shape-memory, i.e., that can be straightened or bent out of its original shape upon exertion of a force and is capable of substantially returning to its original shape upon removal of the force. On suitable material for the support member 54 is a nickel/titanium alloy. Such alloys typically comprise about 55% nickel and 45% titanium, but may comprise from about 54% to about 57% nickel with the balance being titanium. A suitable nickel/titanium alloy is Nitinol, which has excellent shape memory, together with ductility, strength, corrosion resistance, electrical resistivity and temperature stability.

Figure 34:
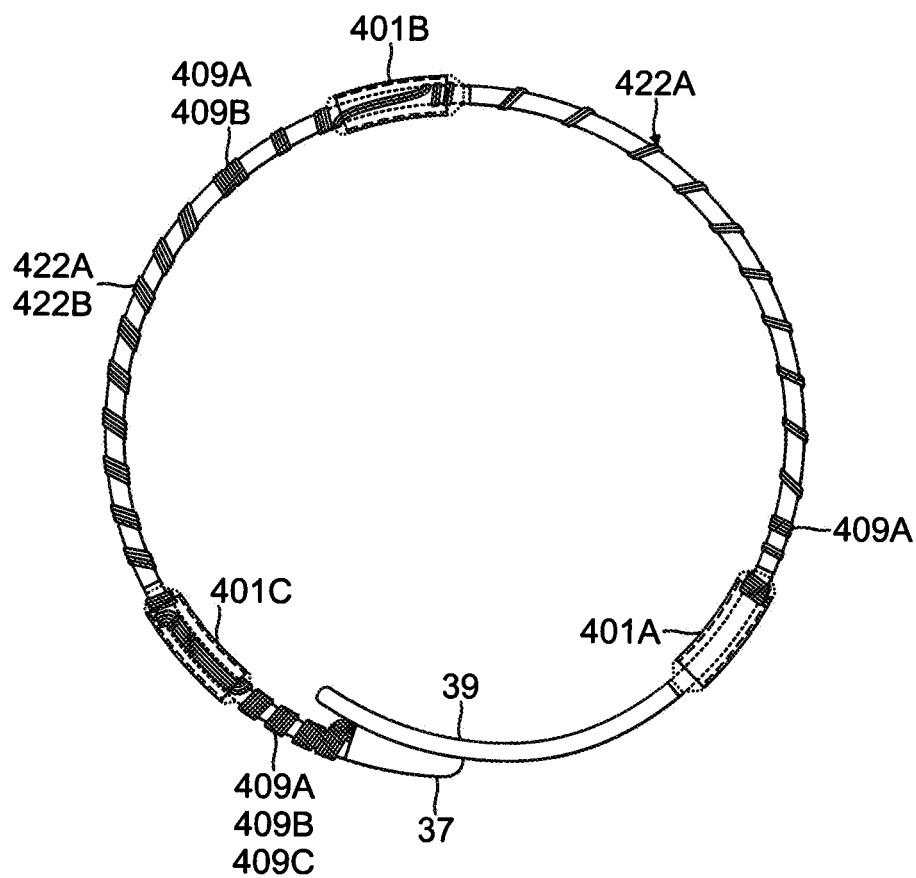
FIG. 34 is a top plan view of an embodiment of a nonlinear SAS assembly in accordance with the present invention.
Figure 35:
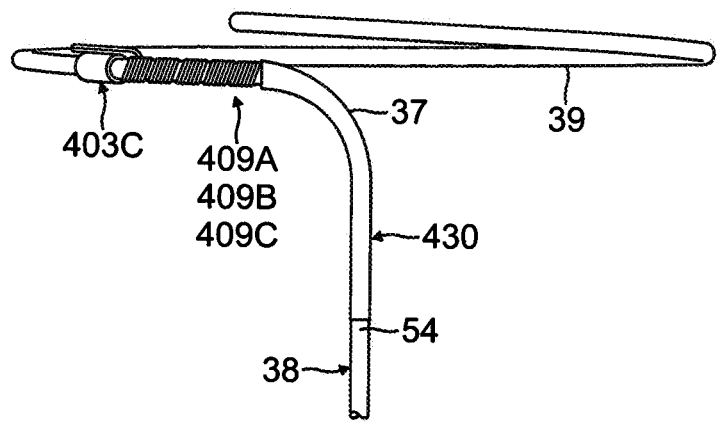
FIG. 35 is a side view of an embodiment of a proximal single axis sensor of a nonlinear SAS assembly in accordance with the present invention.

The support member 54 supports a nonlinear SAS assembly 400 in accordance with a feature of the present invention, an embodiment of which is illustrated in FIGS. 34 and 35. The non-linear SAS assembly 400 carries at least one, if not three or more single axis sensors 401A, 401B, 401C, for sensing location and/or position of the mapping assembly 17. The sensors enable the mapping assembly carrying the non-linear SAS assembly to be viewed under mapping systems manufactured and sold by Biosense Webster, Inc., including the CARTO, CARTO XP and NOGA mapping systems.

The disclosed embodiment includes three single-axis sensors positioned at equi-distance from each other along the generally circular main region 39. The proximal sensor 401C is immediately distal of the elbow 37. A mid-sensor 401B is about 120 degrees from the proximal sensor. A distal sensor 401A is about 120 degrees from the mid-sensor.

Figure 31:
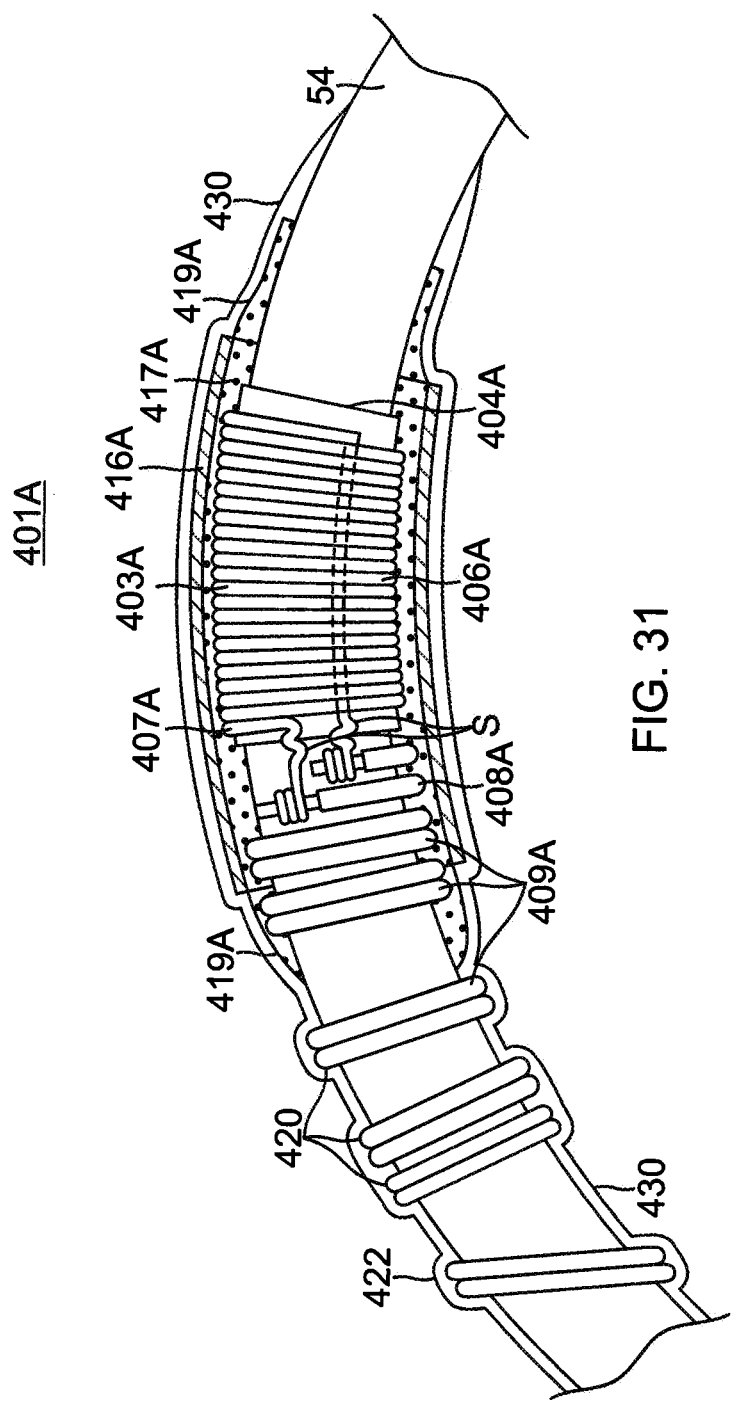
FIG. 31 is a side view of an embodiment of a distal single axis sensor of a nonlinear SAS assembly in accordance with the present invention.

As shown in the embodiment of FIG. 31, the distal sensor 401A includes a conducting member 403A, e.g., a wire, that is wound repeatedly around a predetermined length of a nonconductive tubing 404 surrounding the support member 54 to form a sensing coil as understood by one of ordinary skill in the art. A distal section 406A of the wire extends proximally under the coil 403A. The distal section 406A and a proximal section 407A of the wire both extend proximally past the coil 403A and are each joined, e.g., by wrapping and/or soldering, to a respective exposed distal end of a wire encased in a respective dual side-by-side wire cable 408A at a joint region located just proximal of the coil 403A and the tubing 404A. In the joint region are strain relief adaptations, including the provision at each end of the wire a predetermined amount of slack S proximal in the joint region so as to minimize the risk of breakage and detachment at the soldering joint. Moreover, the cable 408A includes multiple windings of the cable 409A, generally transverse, for example, at least two consecutive 720 degrees, around the support member 54 to anchor the soldered joints between the coil wire and the cable. A protective tubing 416, for example, of polyimide, of sufficient length is placed over the tubing, coil, soldering joints and the most distal strain relief 720 degree winding for sensor 403A. Epoxy, UV glue and/or similar material 417 is injected into the tubing to fill the space between the tubing and the components of the sensor, with excess epoxy extending distally and proximally of the tubing to form end caps 419A around the encapsulated single axis sensor. The proximal end cap may cover the strain relief 720 degree winding proximal of the most distal strain relief 720 degree winding. The epoxy provides further support to each encapsulated single axis sensor by potting and fixing the respective coils and the strain reliefs onto the tubing and in the heat shrink sleeve. The epoxy provides an added degree of rigidity to the encapsulated single axis sensor as further protection against breakage and detachment of the coil wires and the sensor cable. Proximal the encapsulated single axis sensor are additional strain relief 720 degree windings 420A of the cable. Further proximal are looser (e.g., diagonal) windings 422A of the cable around the support member 54.

Figure 32:
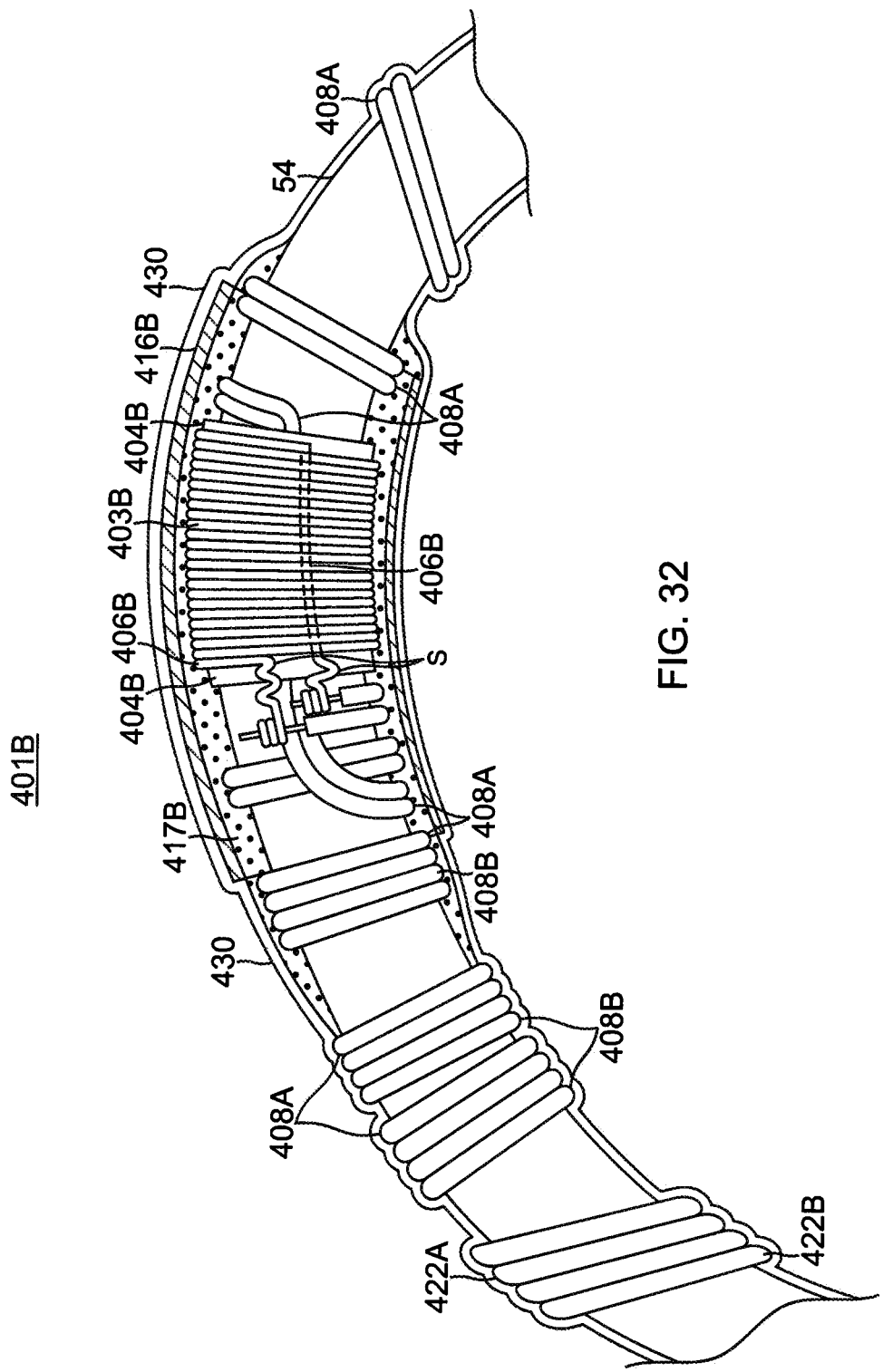
FIG. 32 is a side view of an embodiment of a mid single axis sensor of a nonlinear SAS assembly in accordance with the present invention.
Figure 33:
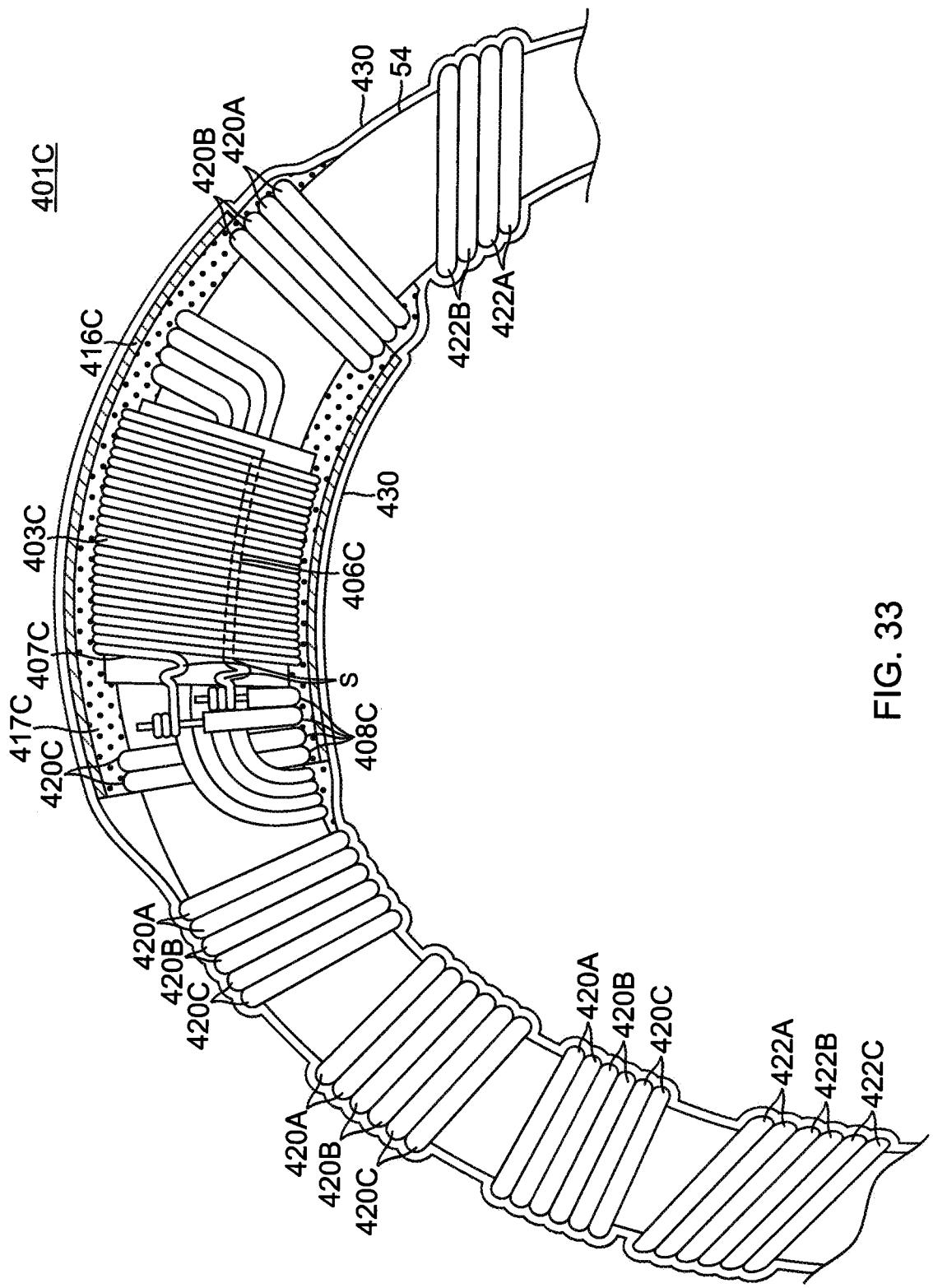
FIG. 33 is a side view of an embodiment of a proximal single axis sensor of a nonlinear SAS assembly in accordance with the present invention.

The mid single axis sensor 403B and the proximal single axis sensor 403A are formed in a similar manner with a similar structure. However, as shown in the embodiments of FIGS. 31 and 32, the dual wire cable 408 from the more distal single axis sensor(s) extend under the non-conductive tubing 404 and thus are insulated and isolated from each sensor coil 403. Proximal of the coils, the cables 408 are jointly wound transversely and diagonally as desired or appropriate proximally toward the elbow 37 of the mapping assembly 17.

Extending over all three single axis sensors between a location immediately distal of the distal single axis sensor 401A and proximal of the elbow 37 but distal of the proximal end of the support member 54 is an outer non-conductive heat shrink sleeve 430.

In manufacturing the non-linear SAS assembly 400, the distal encapsulated SAS 401A is formed, followed by the mid encapsulated SAS 401B, and then the proximal SAS. 401C The outer heat shrink sleeve 430 is then placed over all three SASes. The assembly 400 is sufficiently flexible to allow expansion or contraction of the mapping assembly 17 as needed or appropriate and the assembly 400 is ready for mounting of ring electrodes 26, as described below.

The cables 408A, 408B, and 408C extend proximally from the assembly 400 through the tubing 52 of the assembly 17 exiting the proximal region 38, through the lumen 32 of the intermediate section 14 and through the central lumen 18 of the catheter body 12. The cables 408A, 408B and 408C can extend through a protective, nonconductive sheath 413.

Figure 11:
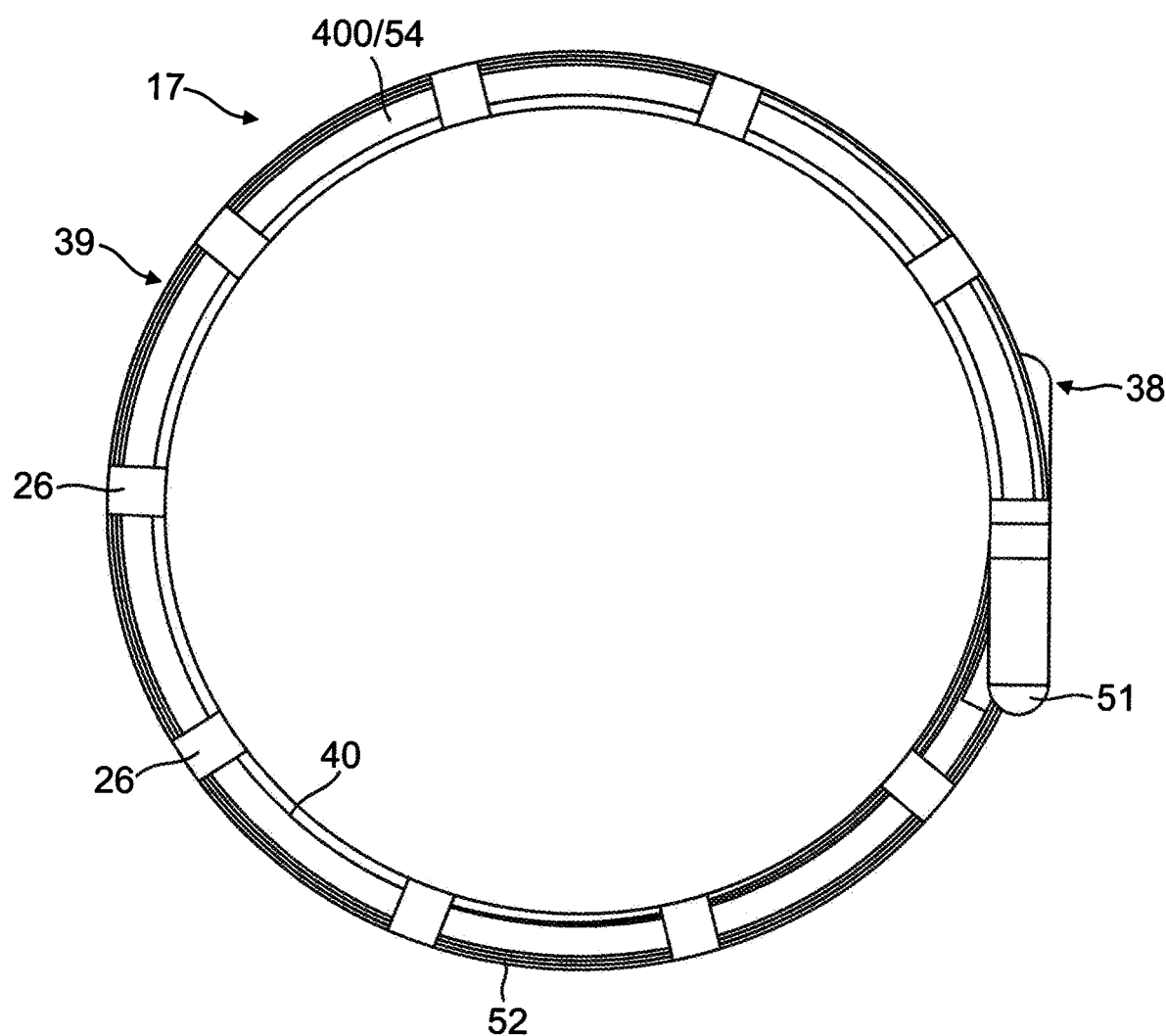
FIG. 11 is a schematic view of the mapping assembly showing one arrangement of the ring electrodes.

The assembly 400 is inserted into the nonconductive cover 52 to extend therethrough. A series of ring electrodes 26 are mounted on the non-conductive cover 52 forming the generally circular main region 39 of the mapping assembly 17, as shown in FIG. 11. The ring electrodes 26 can be made of any suitable solid conductive material, such as platinum or gold, or a combination of platinum and iridium, and mounted onto the non-conductive cover 52 with glue or the like. Alternatively, the ring electrodes 26 can be formed by coating the non-conductive cover 52 with an electrically conducting material, like platinum, gold and/or iridium. The coating can be applied using sputtering, ion beam deposition or an equivalent technique. A suitable mapping assembly is described in U.S. Pat. No. 7,274,957, the entire disclosure of which is hereby incorporated by reference. If desired, additional electrodes (not shown) could be mounted along the intermediate section 14 and/or the generally straight proximal section 38.

The contraction puller member 35, for example, a contraction puller wire, is provided to contract the generally circular main region 39 to thereby change or reduce its diameter, for example, when mapping or ablating circular or tubular regions of the heart. The contraction wire 35 has a proximal end anchored in the control handle 16, which is used to manipulate the contraction wire as described further below. The contraction wire 35 extends through the central lumen 18 of the catheter body 12, through the third lumen 32 of the intermediate section 14 and into the non-conductive cover 52 of the mapping assembly 17. The portion of the contraction wire 35 extending through the non-conductive cover 52 is positioned on the side of the generally circular main region 39 closer to the center of the generally circular main region, as best shown in FIG. 6. The center of the generally circular main region refers to the center of the circle formed by the generally circular main region. With this arrangement, contraction of the generally circular main region 39 is dramatically improved over arrangements where the position of the contraction wire 35 is not so controlled.

Figure 12:
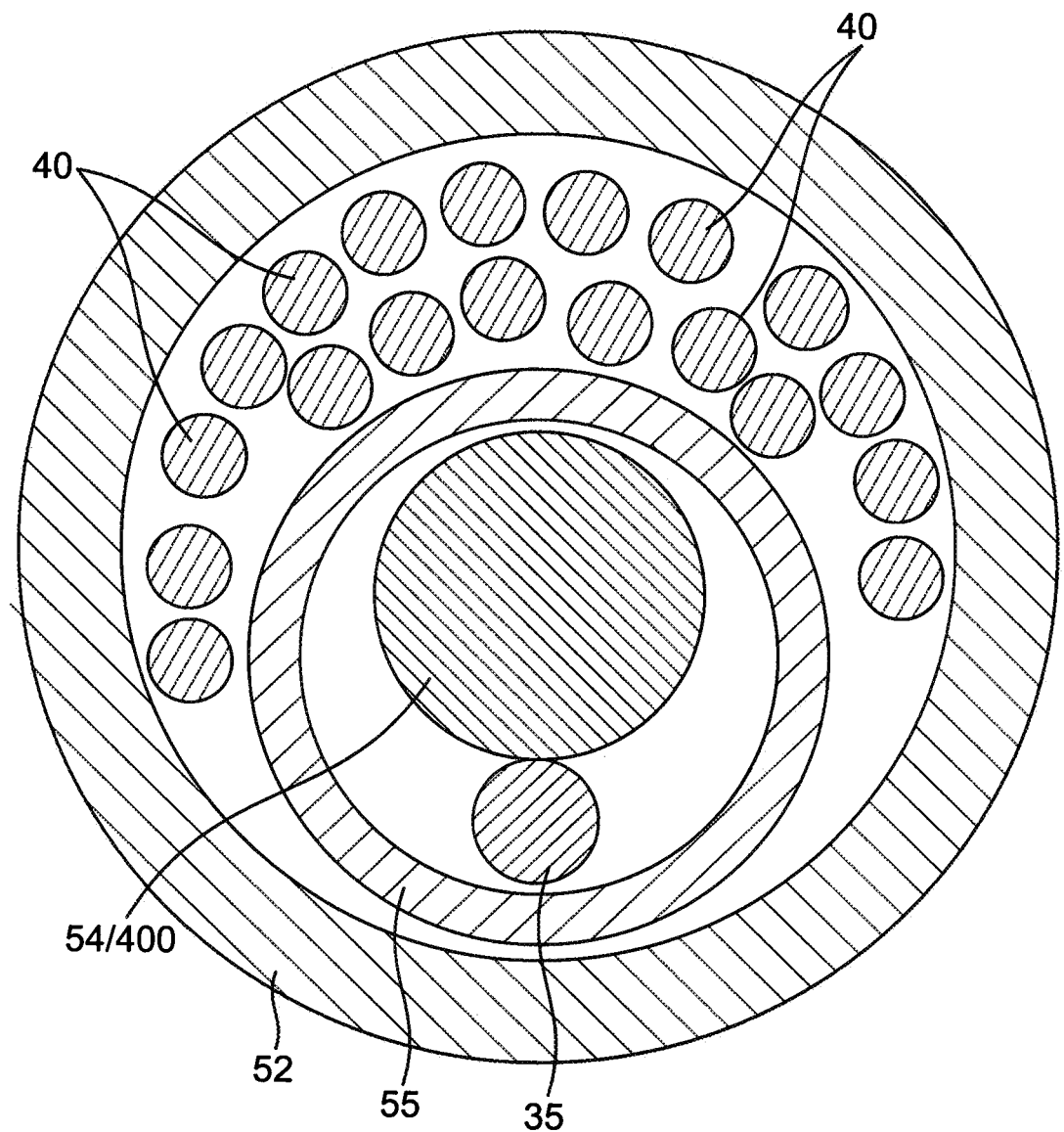
FIG. 12 is a longitudinal cross-sectional view of the mapping assembly of FIG. 9, taken along line 12-12.
Figure 13:
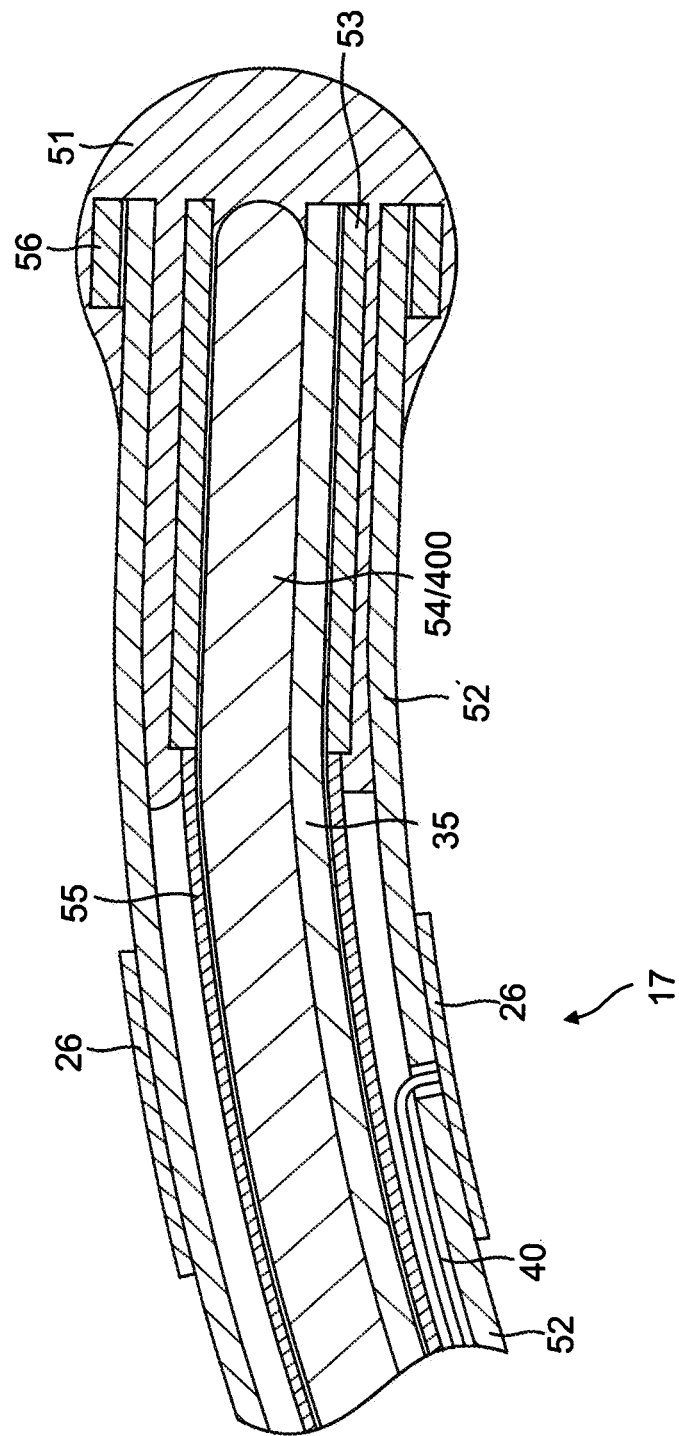
FIG. 13 is a side cross-sectional view of an embodiment of a distal end of the mapping assembly of FIG. 9.
Figure 14A:
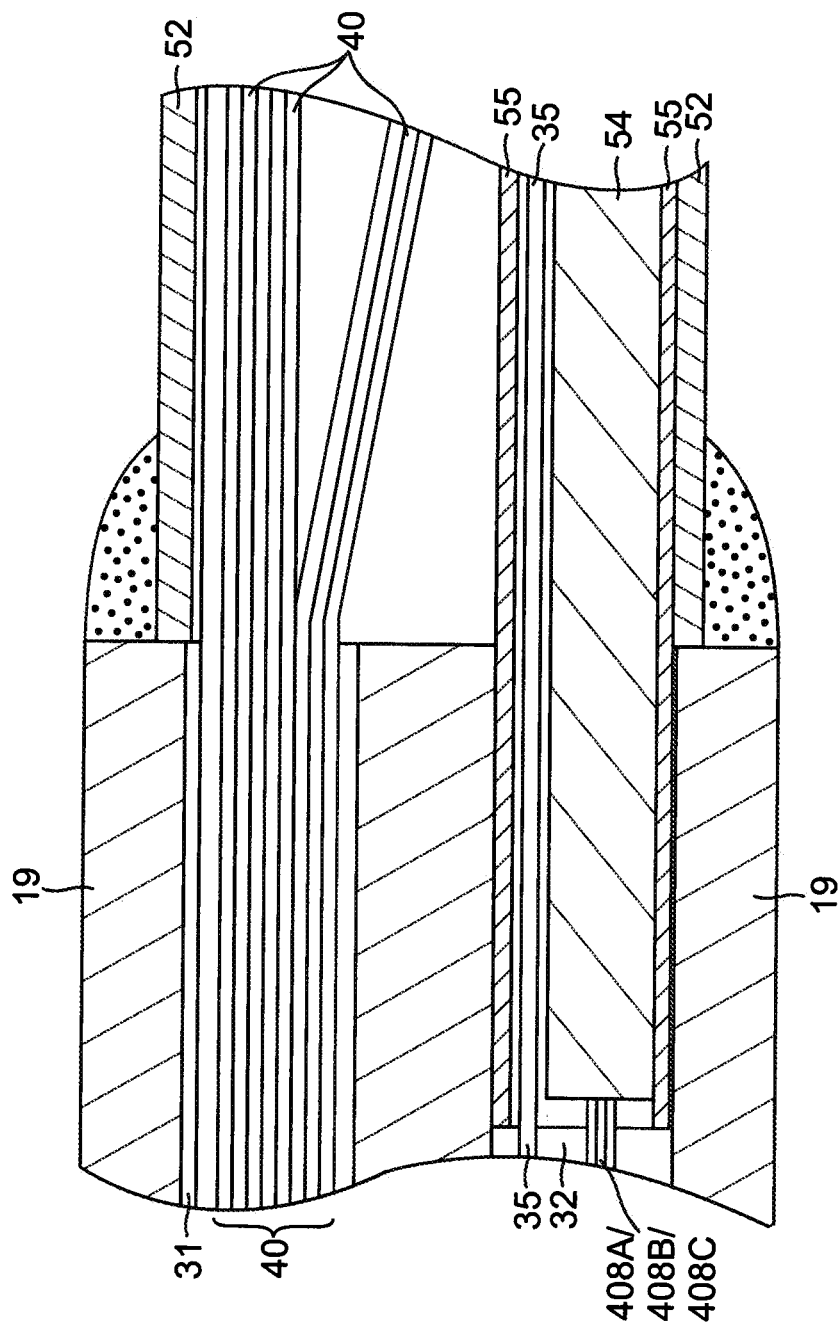
FIG. 14A is a side cross-sectional view of an embodiment of a junction between the intermediate section and the mapping assembly, taken along a first diameter.

As shown in FIGS. 11 and 12, within the mapping assembly 17, the contraction wire 35 extends through a plastic tube 55. In one embodiment, the plastic tube 55 comprise three layers, including an inner layer of polyimide over which a braided layer is formed, the braided layer comprising a braided stainless steel mesh or the like, as is generally known in the art. The braided layer enhances the strength of the plastic tube 55, reducing the tendency for contraction wire 35 to straighten the preformed curve of the mapping assembly 17. A thin plastic layer of polytetrafluoroethylene is provided over the braided layer to protect the braided layer from getting tangled with the lead wires 40 within the non-conductive cover 52. The plastic tube 55 has a proximal end anchored to the distal end of the intermediate section 14 in the third lumen 32 by glue or the like (FIG. 14A). The support member 54 extends through the plastic tube 55 with the contraction wire 35 (FIG. 14A). The distal ends of the support member 54 and the contraction wire 35 are soldered or otherwise attached to a small stainless steel tube 53 (FIG. 13). With this arrangement, the relative positions of the contraction wire 35 and the support member 54 can be controlled so that the contraction wire can be positioned on the side of the generally circular region 39 closer to the center of the generally circular region 39, as described above. The contraction wire 35 on the inside of the curve pulls the support member 54 to the inside of the curve, enhancing contraction of the generally circular region 39. Further, when the plastic tube 55 includes a braided layer, it keeps the contraction wire 35 from tearing through the non-conductive cover 52.

A third compression coil 46 is situated within the catheter body 12 and intermediate section shaft 14 in surrounding relation to the contraction wire 35 (FIG. 8A). The third compression coil 46 extends from the proximal end of the catheter body 12 to near the distal end of the third lumen 32 of the intermediate section 14. The third compression coil 46 is made of any suitable metal, e.g., stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 68, e.g., made of polyimide tubing. The third compression coil 46 can be formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the mapping assembly 17 as it absorbs more of the compression.

The third compression coil 46 is anchored at its proximal end to the outer wall 20 of the catheter body 12 by the proximal glue joint 50 and to the intermediate section 14 by distal glue joint 72.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

In the depicted embodiment of FIG. 13, the distal end of the mapping assembly 17 is sealed closed with a dome 51 of polyurethane glue or the like. A short ring 56, made of metal or plastic, and e.g., polyamide, is mounted within the distal end of the non-conductive cover 52. The short ring 56 prevents the distal end of the non-conductive cover 52 from collapsing, there by maintaining the diameter of the non-conductive cover at its distal end.

Figure 14B:
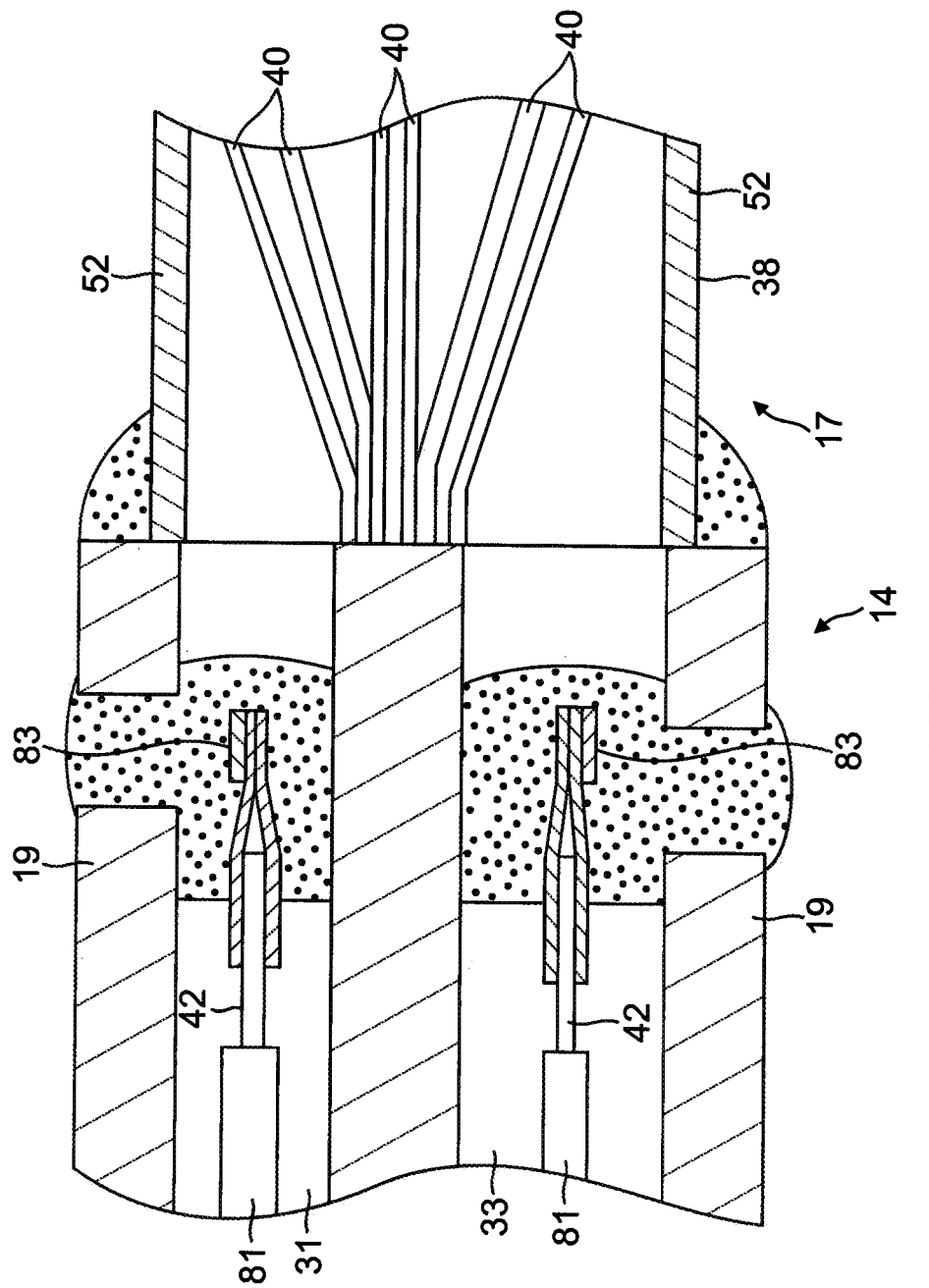
FIG. 14B is a side cross-sectional view of the junction between the intermediate section and the mapping assembly, taken along a second diameter generally perpendicular to the first diameter.

At the junction of the intermediate section 14 and the mapping assembly 17 as shown in FIGS. 14A and 14B, the non-conductive cover 52 is attached to the intermediate section 14 by glue or the like. The plastic tube 55 has its proximal end inserted and glued in the distal end of the intermediate section 14. The glue (not shown) from the plastic tube 55 can further serve to anchor the distal end of the third compression coil 46 in place within the third lumen 32. The support member 54 extends from the third lumen 32 into the plastic tube 55 within the non-conductive cover 52. The proximal end of the support member 54 terminates a short distance proximally from the distal end of the third lumen 32, approximately about 5 mm, so as not to adversely affect the ability of the intermediate section 14 to deflect. However, if desired, the proximal end of the support member 54 can extend proximally further into the intermediate section 14 and/or the catheter body 12.

The lead wires 40 attached to the ring electrodes 26 extend through the first lumen 30 of the intermediate section 14 (FIG. 8A), through the central lumen 18 of the catheter body 12, through the control handle 16, and terminate at their proximal end in a connector (not shown) which is connected to an appropriate monitor or other device for receiving and displaying the information received from the ring electrodes 26. The portion of the lead wires 40 extending through the central lumen 18 of the catheter body 12, control handle 16 and proximal end of the intermediate section 14 is enclosed within a protective sheath 62, which can be made of any suitable material, such as polyimide. The protective sheath 62 is anchored at its distal end to the proximal end of the intermediate section 14 by gluing it in the lead wire lumen 30 with polyurethane glue or the like to form glue joint 73.

The lead wires 40 are attached to the ring electrode 26 by any conventional technique. In one embodiment, each ring electrode 26 is mounted by first forming a hole in the non-conductive cover 52. An electrode lead wire 40 is fed through the hole, and the ring electrode 26 is welded in place over the lead wire and non-conductive cover 52.

With reference to FIG. 7, the control handle 16 comprises a generally elongated handle housing, which can be made of any suitable rigid material, such as plastic configured through a suitable molding process. In the illustrated embodiment, the housing includes two opposing halves 16a and 16b that generally mirror each other and are joined by glue, sonic welding or other suitable means along a longitudinal peripheral seam 28 around the housing. In the illustrated embodiment, the cross section of the handle 16 formed by the opposing halves changes along the length of the handle. A more distal portion 112 has a smaller, generally rectangular cross section. A mid-portion 114 has a larger, generally rectangular cross section. A more proximal portion 116 has a generally circular cross section.

In the illustrated embodiment of FIGS. 1 and 9, the control handle 16 houses components of a deflection control assembly 74 in the mid-portion 114. The deflection control assembly includes a deflection member or arm 75 that can be directly manipulated by an operator to control deflection of the intermediate section 14. The deflection arm 75 is rotatable about an axis 76 that is generally transverse or perpendicular to the longitudinal axis of the control handle. The deflection control assembly 74 has a rotatable rocker member 78 that acts on the deflection puller members 42 to deflect the intermediate section 14.

The rocker member 78 has a length L dimension, a width W dimension and a thickness T dimension (FIGS. 10 and 11). Along its thickness dimension T, the rocker member 78 is configured with two opposing annular formations 140a and 140b that define a central hole or passage 143 that extends through its entire thickness. The central hole 143 is aligned with the rotational axis 76 of the deflection arm 75. Along its length dimension L, the rocker member 78 also has two smaller holes 146 that oppose each other across the central hole 143. In each hole sits a pulley 147, for example, a snap bearing (FIG. 12), that has a rotational axis parallel to the axis 76. Each deflection puller member 42 enters the rocker member through slots 148 and a portion is wound around a respective pulley 147.

As understood by one of ordinary skill in the art, the rocker member 78 and the pulleys 147 are arranged such that rotation of the rocker member in one direction about the axis 76 draws back one puller member 42 to deflect the intermediate section 14 in that direction. With reference to FIGS. 20A-20C, as the rocker member 78 is rotated by means of the deflection arm (as represented by line 75), the pulleys 147 are displaced from a neutral position (FIG. 20A) with one pulley 147 drawing a puller member 42 on one side of the catheter body 12 against its anchored proximal end for deflecting the intermediate section 14 toward that side (FIGS. 20A-20C).

Each deflection puller member 42 may comprise multiple segments. As illustrated in FIG. 9, each deflection puller member has a distal puller wire 42a and a proximal fiber 42b that are joined or connected at a location within the control handle 16 distal the rocker member 78. The puller wire 42a and the tensile fiber 42b of each deflection puller member are connected or secured to each other by a connector 154, e.g., a crimped brass ferrule covered by shrink tubing. Each puller wire 42a extends through the catheter body 12 and the intermediate section 14. Each tensile fiber 42b extends inside the control handle 16. In this manner, it is the more flexible tensile fibers 42b that interact with the pulleys 147 and undergo repeated bending and straightening during deflection operations, as they are less prone to bending stress and fatigue failure.

Each puller wire 42a is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Each tensile fiber 42b may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions.

In the illustrated embodiment of FIG. 9, each tensile fiber 42b extends proximally from the connector 154 toward the rocker member 78 where each is wound around a respective pulley 147 and turns about 180 degrees to double back toward the distal end of the control handle. Each proximal end of the tensile fiber 42b is anchored by an anchor assembly 90 that includes a pair or racks 92, a slug 94 and a stop 96. The proximal end of each tensile fiber 22b extends between a channel 91 defined by the pair of racks 92, and the proximal end of each tensile fiber is encased within a molded member or slug 94 sized to fit in and translate in the channel 91. Proximal the slug are the stops 96 that are adjustably positioned in a selected location along the racks 92, for example, by means of interlocking teeth 98 formed in the racks and the stops to releasably lock in the selected position against movement. The stops 96 are formed so that each respective tensile fiber 42b can slide through or below them while blocking the slugs 94 from moving proximally past them. Accordingly, the stops 96 limit the proximal movement of the slugs 94 and anchor the proximal ends of the tensile fibers 42b to effectuate deflection when each is drawn proximally by the deflection control assembly 74. During assembly of the control handle 16, before the two housing halves 16a, 16b are joined, the stops 96 are selectively positioned between the racks 92 to achieve a desirable tension in each tensile member. The interlocking teeth 98 of the racks 92 and stops 96 allow for fine adjustments in setting the tension.

The construction and assembly of the deflection control assembly 74 including the deflection arm 75 and a tension adjustment member 101 on the control handle 16 are described as follows. With reference to FIGS. 14A and 14B, the rocker member 78 of the assembly 74 is situated between the two halves 16a and 16b of the control handle 16, with each of its annular formations 140a and 140b extending respectively through an opening 120a, 120b formed in the distal portion 114 of each housing half 16a and 16b.

Figure 15:
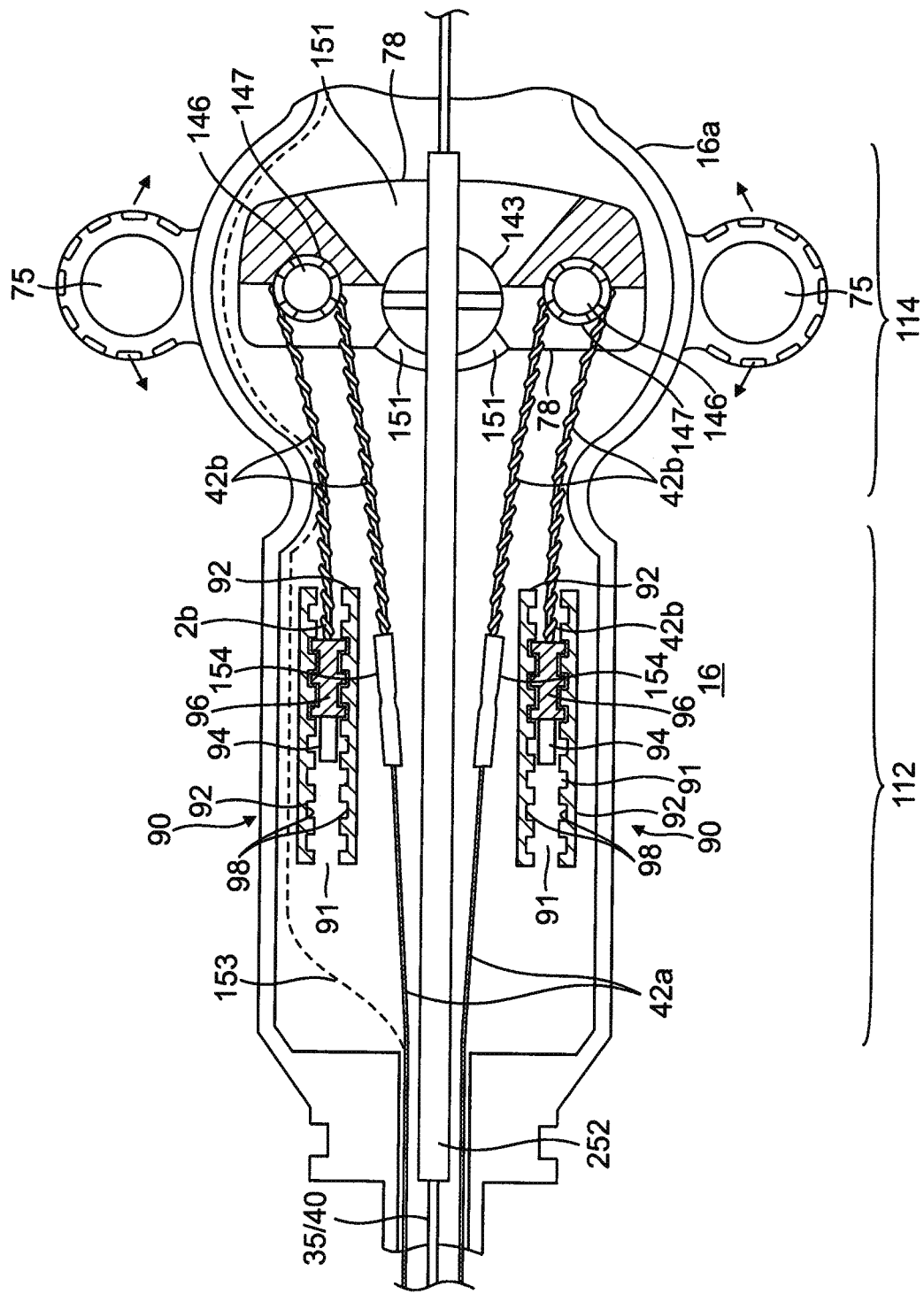
FIG. 15 is a top plan view of an embodiment of a control handle housing half including an embodiment of a deflection control assembly.
Figure 16:
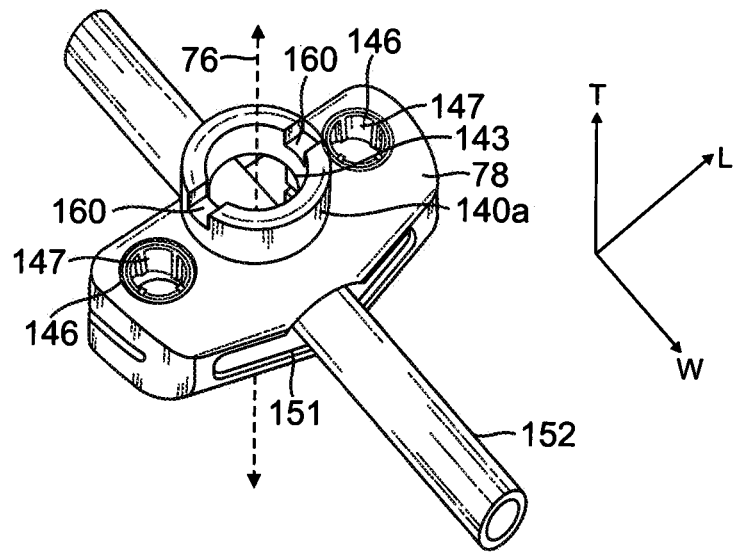
FIG. 16 is a top perspective view of an embodiment of a rocker member of a deflection control assembly.

The annular formation 140a has recesses 160 (FIG. 10) exposed through the opening 120a (FIG. 15) that receive protrusions 152 projecting from a facing surface 154 of the deflection arm 75 (FIG. 16) to rotationally couple the deflection arm 75 and the rocker member 78. The protrusions 152 can snap fit into the recesses 160 and/or be secured by adhesives, glue, sonic welding and the like. A central circular protrusion 156 from the deflection arm 75 fits into the hole 143 circumscribed by the annular formation 140a of the rocker member 78. A suitable deflection assembly and control handle are described in U.S. application Ser. No. 12/346,834, published as U.S. Publication No. 2010/0168827, the entire disclosure of which is hereby incorporated by reference. Another suitable deflection assembly with deflection sensitivity is described in U.S. application Ser. No. 12/211,728, published as U.S. Publication No. 2010/0069834, the entire disclosure of which is hereby incorporated by reference. Therein, a cam that is responsive to a deflection sensitivity knob can vary the separation distance between the two pulleys 147, thereby changing the deflection sensitivity of the deflection arm.

Opposing the deflection arm 75 is the deflection tension adjustment member or dial 101 (FIGS. 17 and 20) which is coupled to and indirectly engaged with the rocker member 78 by various mechanisms and parts and allows an operator to adjust the ease with which the deflection arm 75 can be rotated. Mounted primarily on the housing half 16b, the illustrated embodiment of a tension adjustment assembly 100 includes the adjustment dial 101 (FIG. 17), a locking plate 102 (FIG. 18), a tension cap screw 103, a retaining nut 136 and a washer 119 (see FIGS. 14A and 14B). A user rotates the dial 101 to adjust the tightness or tension of the rotational movement of deflection arm 75 by effectively compressing or releasing the rocker member 78 against the washer 119 (e.g., a Belleville type) and the control handle housing half 16b.

Figure 17:
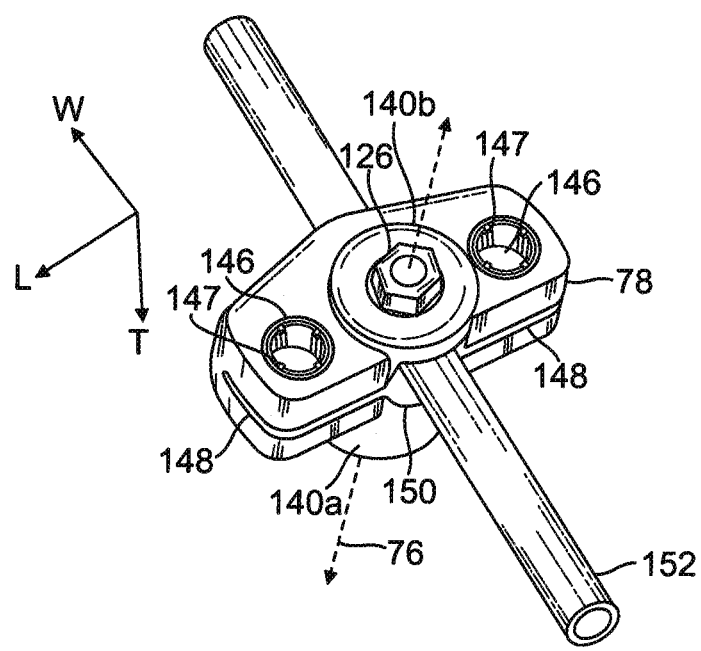
FIG. 17 is a bottom perspective view of an embodiment of a rocker member.
Figure 18:
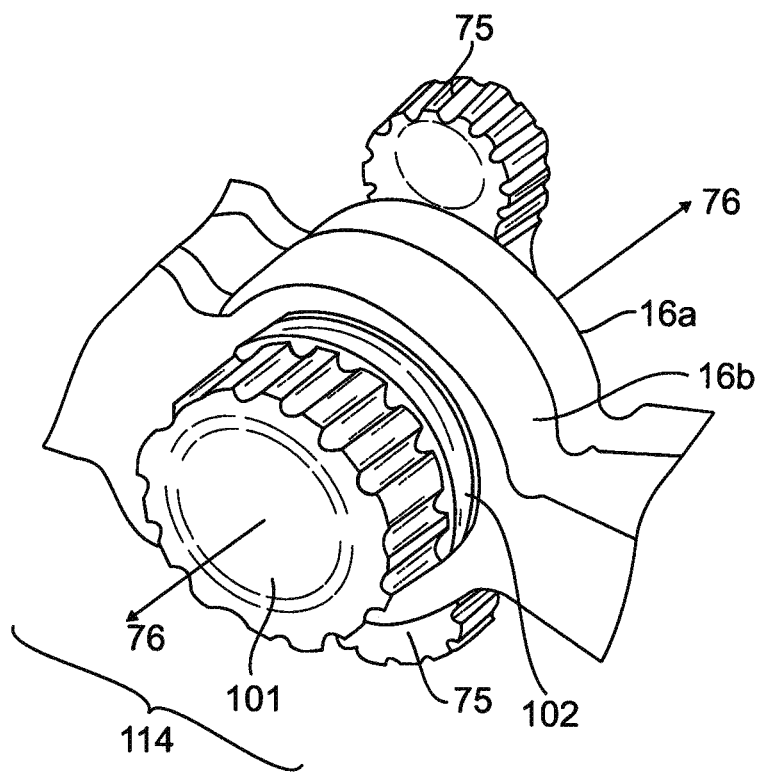
FIG. 18 is a partial perspective view of a portion of an embodiment of a deflection arm and a tension control member mounted on a control handle.

The dial 101 has a generally circular cross section with a circumferential edge 115 having a friction-inducing surface (FIG. 17). A central circular protrusion 105 and a plurality of prongs 106 (FIG. 17) situated along a diameter of the dial project from a surface 104 of the dial 101.

Figure 19:
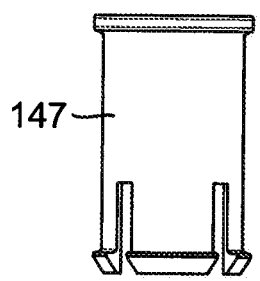
FIG. 19 is a side view of an embodiment of a pulley of a deflection control assembly.
Figure 20:
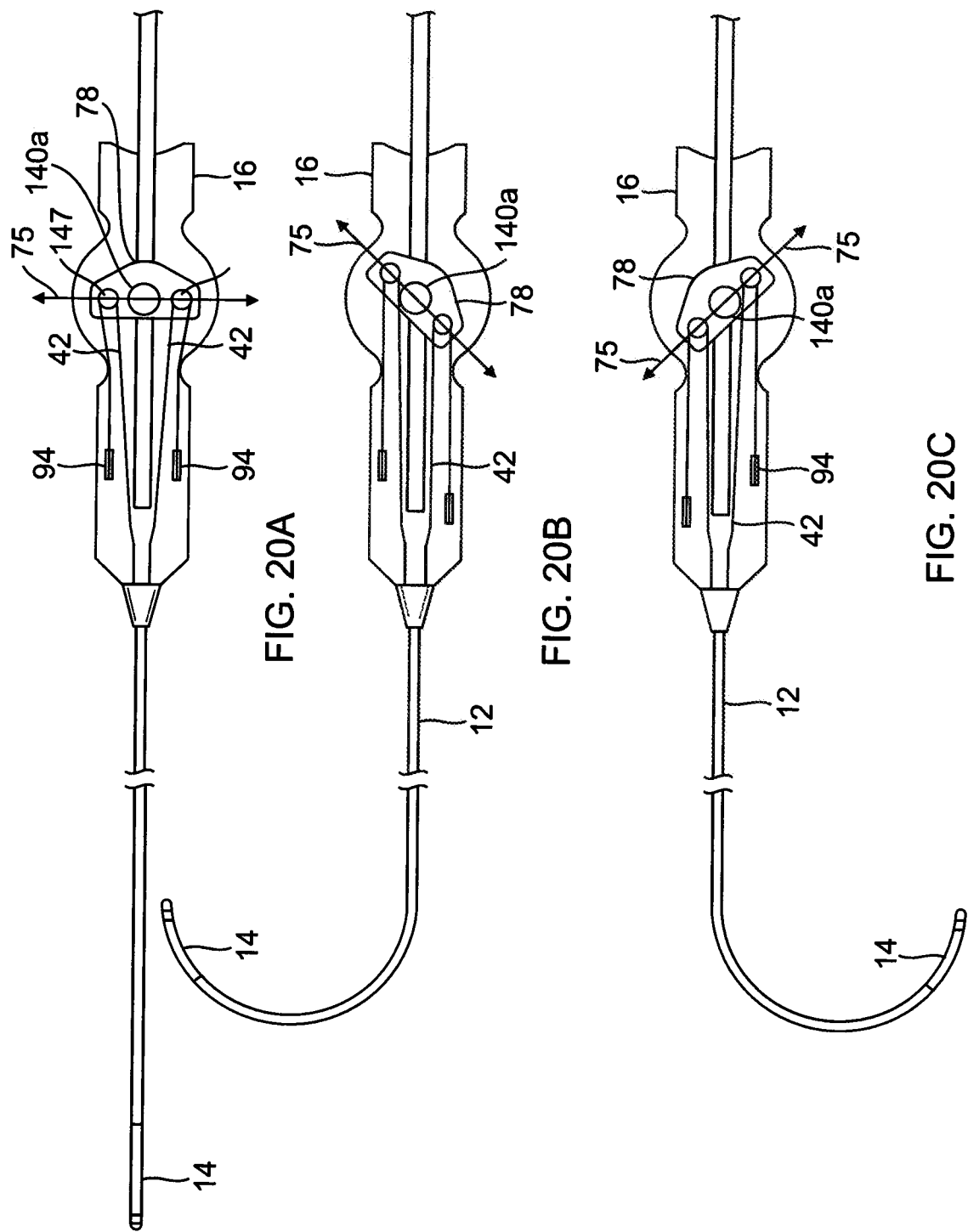
FIGS. 20A-20C are schematics of an embodiment of the deflection control assembly in neutral and rotated configurations.
Figure 21:
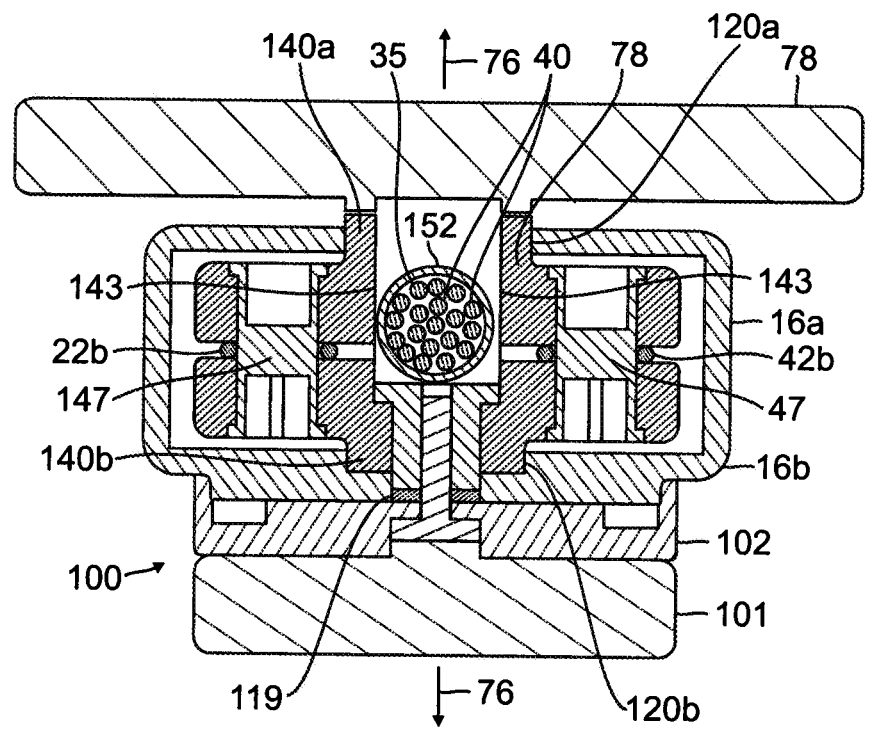
FIG. 21 is a longitudinal cross section of an embodiment of the deflection control assembly and tension control assembly mounted on a control handle.
Figure 21A:
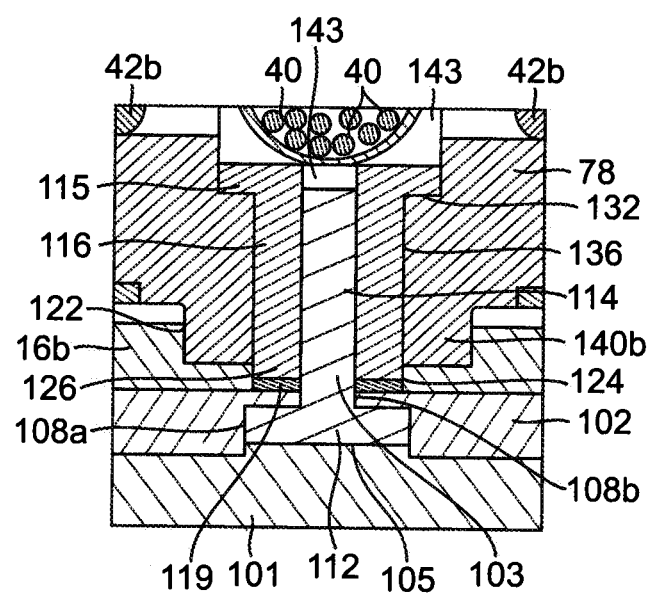
FIG. 21A is a detailed view of a portion of FIG. 21, including an embodiment of a retaining nut and a tension screw.
Figure 22:
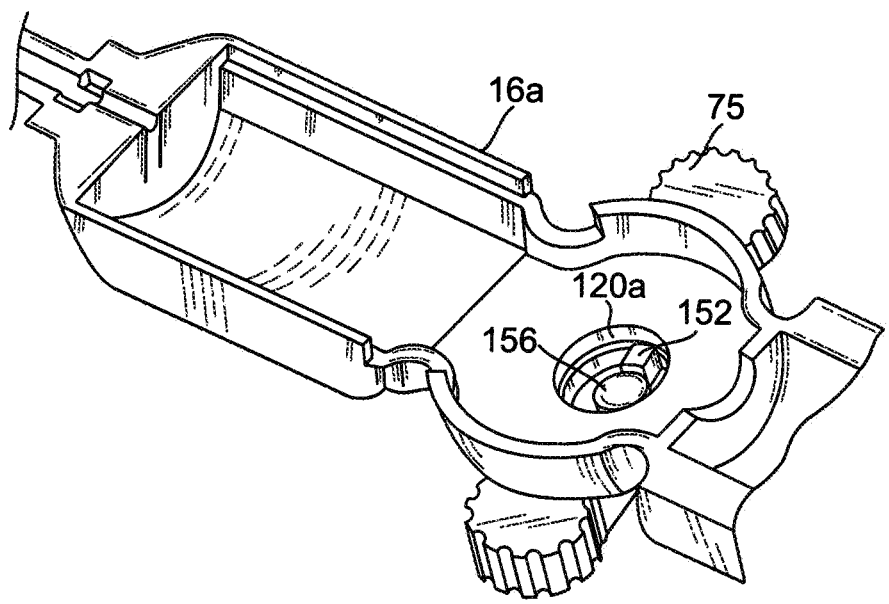
FIG. 22 is a partial perspective view of an embodiment of a first control handle housing half.

The locking plate 102 is sandwiched between the dial 101 and the handle housing 16b (FIG. 20). The locking plate 102 (FIG. 18) has a central larger hole 107 and two smaller holes 108, all three of which extend through the entire thickness of the locking plate. The two prongs 106 of the dial 101 are adapted to be inserted through the smaller holes 108 in the plate 102 (FIG. 21) and received in semi-circular grooves 109 (FIG. 19) formed in an outer surface of the housing half 16b. The grooves 109 limit the degree of rotation of the dial 101 in clockwise and counterclockwise directions. The central hole 107 of the plate 102 (FIG. 18) has different cross-sections that include a larger circular cross-section 107a and a smaller circular cross-section 107b. The larger circular cross-section 107a receives a head 112 of a cap screw 103, and the smaller circular cross-section 107b receives a threaded body 115 of the cap screw 103 (FIG. 14a).

The threaded body 115 of the cap screw 103 extending through the central hole 107 of the locking plate 102 engages the retaining nut 136 situated in the opening 143 of the rocker member 78. A head 115 of the nut abuts and is anchored against a neck 132 formed in the inner surface of the opening 143 of the rocker member 78. The opening 120b in the housing half 16b (FIG. 21) has a larger cross section 122 and a smaller cross section 124. The smaller cross section 124 has a polygonal shape which matches a polygonal (e.g., hexagonal) end 126 of the nut 136 so that the nut 136 is effectively locked against rotation relative to the housing handle 16b.

The central protrusion 105 of the dial 101 (FIG. 17) forms a press or interference fit with the head 112 of the cap screw 103 to create rotational alignment between these two components. The prongs 106 of the dial 101 lock and rotationally couple the dial 101 and the lock plate 102, and the cap screw 103 is rotationally coupled to the locking plate 102. Coupling of the dial 101 and the locking plate 102 may also be achieved by means of welding the two components together. In that case, the prongs 106 need not protrude from the dial 101 but can instead extend from the locking plate 102.

Between the polygonal end 126 of the nut 136 and the housing handle 16b is the washer 119 whose compression against the nut 136 and the housing handle 16b is adjustable by the user's rotation of the dial 101 which tightens or releases the engagement between cap screw 103 and the nut 136, thus increasing or decreasing the ease with which the rocker member 78 and hence the deflection arm 75 can be rotated.

Components that extend through the control handle, including, for example, the lead wires 40 and the contraction wire 35 also enter the control handle at the distal end. In the illustrated embodiment of FIG. 9, these components extend along the longitudinal axis of the control handle. A protective tubing 152 through which the components extend can be provided, positioned between the two deflection puller members 42 and through a channel 150 form through the width dimension W of the rocker member 78 (FIG. 11). Distal and proximal portions of the channel 150 have indents, e.g., triangular or wedge-shaped, 151 (FIGS. 9 and 11) to allow the rocker member 78 to rotate freely within a predetermined range of angles, e.g., about ±45 degrees of the longitudinal axis of the control handle 16, without interference by the tubing 152 and the components therethrough.

Alternatively, the components extending through the control handle, with the exception of the contraction wire 35, are routed on an off-axis path 153 diverging from the deflection puller members 42 at entry into the distal end of the control handle 16. The components thus extend along the periphery of the housing handle, bypassing the rocker member 78.

It is understood that the distance between the distal end of the compression coils 44 and the distal anchor sites of each deflection puller members 42 in the intermediate section 14 determines the curvature of the intermediate section 14 in the direction of the deflection puller members. For example, an arrangement wherein the two deflection puller members 42 are anchored at different distances from the distal ends of the compression coils 44 allows a long reach curve in a first plane and a short reach curve in a plane 90 degree from the first, i.e., a first curve in one plane generally along the axis of the intermediate section 14 before it is deflected and a second curve distal to the first curve in a plane transverse, and preferably normal to the first plane. The high torque characteristic of the catheter intermediate section 14 reduces the tendency for the deflection in one direction to deform the deflection in the other direction. Suitable deflection control handles and parts thereof for use with such a catheter are described in U.S. patent application Ser. No. 08/924,611, filed Sep. 5, 1997, now U.S. Pat. No. 6,123,699, Ser. No. 09/130,359, filed Aug. 7, 1998, now U.S. Pat. No. 6,171,277, and Ser. No. 09/143,426, filed Aug. 28, 1998, now U.S. Pat. No. 6,183,463, all of which are incorporated by reference.

For adjusting the mapping assembly 17 by means of a third puller member, e.g., the contraction wire 35, a distal end of the contraction wire extending between the two deflection puller members 42 within the control handle is anchored in the control handle for actuation by means of a rotational control assembly 200. In the illustrated embodiment of FIG. 23, the rotational control assembly 200 includes an outer rotational cam 202, a pulley shaft 204 and a pulley 206 around which the third puller member 35 is wrapped. The cam 202 closely surrounds the proximal portion 116 of the control handle and as the proximal portion 116 has a cylindrical shape, the rotational cam is in a circumferential relationship with the proximal portion so that it can rotate about a longitudinal central axis 205 of the proximal portion 116 on an outer surface 208 of the proximal portion and serve as a rotational interface between the user and internal components of the rotational control assembly 200. In that regard, the outer surface 208 is sufficiently smooth such that the cam 202 can rotate on it with minimal frictional forces. A friction-inducing surface can be provided on an outer surface of the cam 202 to facilitate manipulation and rotation by the user.

The proximal portion 116 under the cam 202 has two diametrically opposing guide slots 208 extending axially in a direction parallel to the longitudinal axis 205 of the proximal portion 116. The cam 202 has on its inner surface two opposing helical tracks or grooves 210 extending about the longitudinal axis 205. The helical grooves 210 are configured such that any plane perpendicular to the longitudinal axis intersects the grooves along a diameter of the proximal portion 116. The shaft 204 extends diametrically between the two guide slots 208, traversing the interior of the proximal portion at an angle generally perpendicular to the longitudinal axis 205. The guide slots 208 are sized so that the shaft 204 can pass through the slots and have each of its two opposing ends 212 be received in a respective helical groove on the inner surface of the cam. As such, the length of the shaft is greater than an outer diameter of the proximal portion 116 but lesser than an outer diameter of the cam 202. Accordingly, the helical grooves 210 are sized to receive the ends 212 and allow the ends to slide therein.

Mounted on the shaft, for example, at or near a midpoint of the length of the shaft, is the pulley 206 on which the third puller member is wrapped. The third puller member which can be any suitable material, including a puller wire or contraction wire, has a proximal end (not shown) that is anchored to the control handle or to any other rigidly mounted component within the control handle, at a location distal of the distal ends of the guide slots. Longitudinal movement of the contraction wire 35 relative to the catheter body 12 can effectuate, for example, contraction and expansion of the mapping assembly 17.

Figure 23:
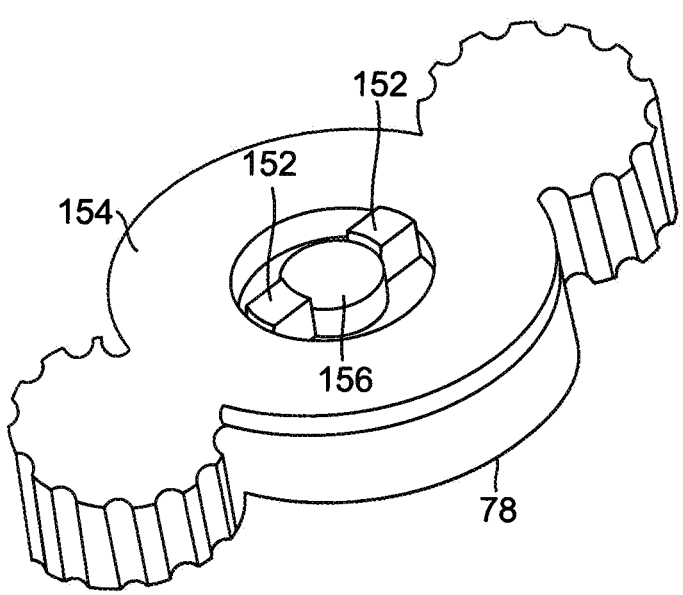
FIG. 23 is a perspective view of an embodiment of a deflection arm.
Figure 24:
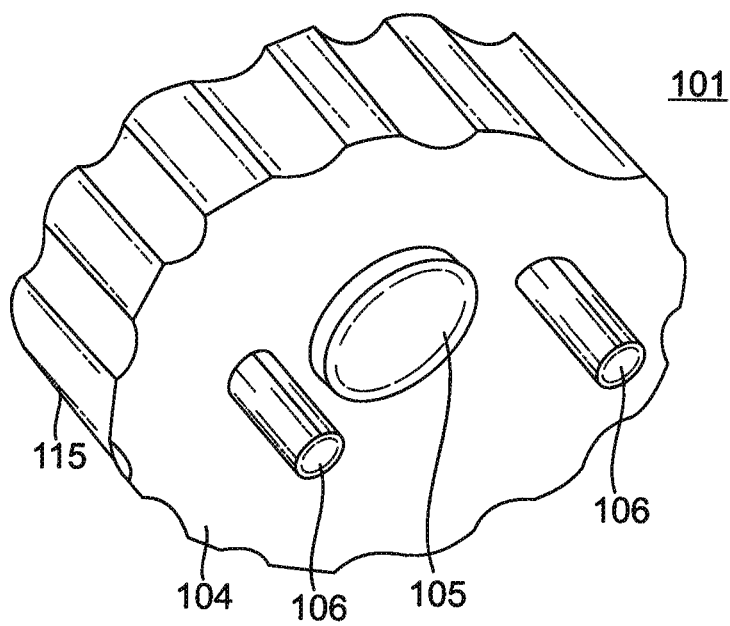
FIG. 24 is a perspective view of an embodiment of a tension control dial.
Figure 25:
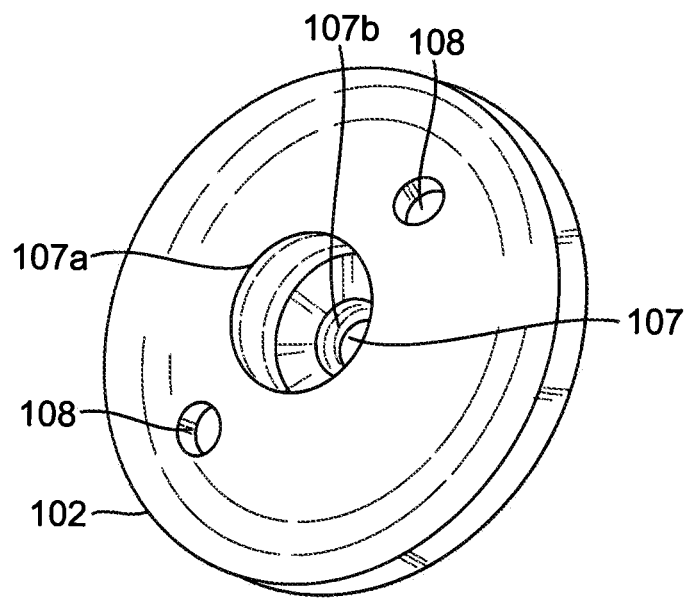
FIG. 25 is a perspective view of an embodiment of a locking plate.
Figure 26:
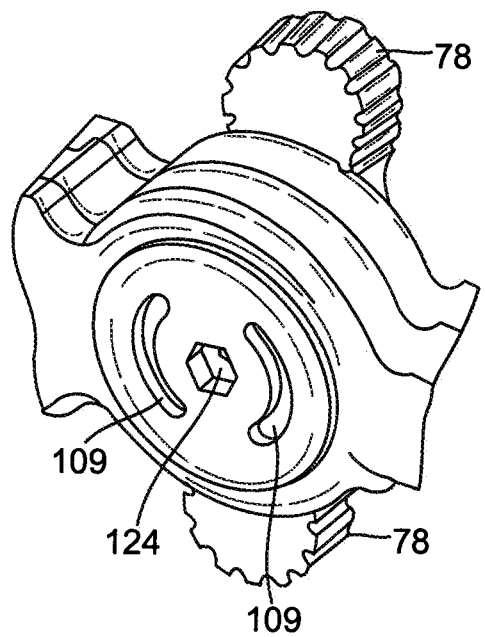
FIG. 26 is a partial perspective view of a portion of an embodiment of a control handle.
Figure 27:
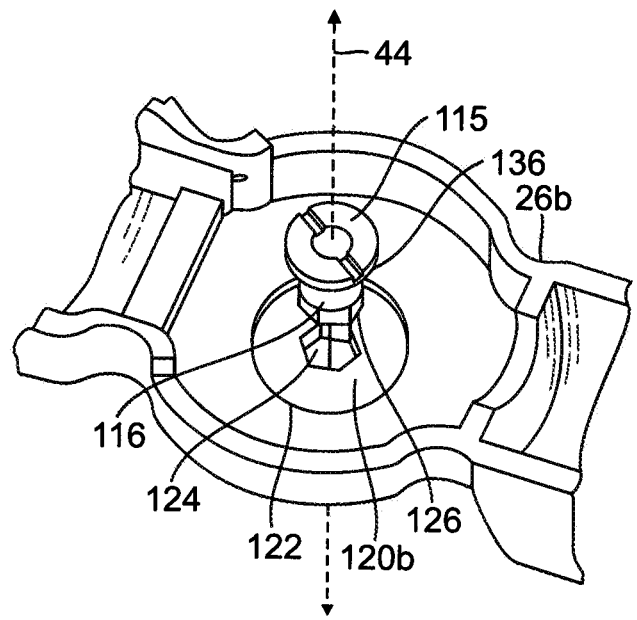
FIG. 27 is a partial perspective view of a portion of an embodiment of a second control handle housing half and a retaining nut, the second control housing half adapted to oppose the first control handle housing half.
Figure 28:
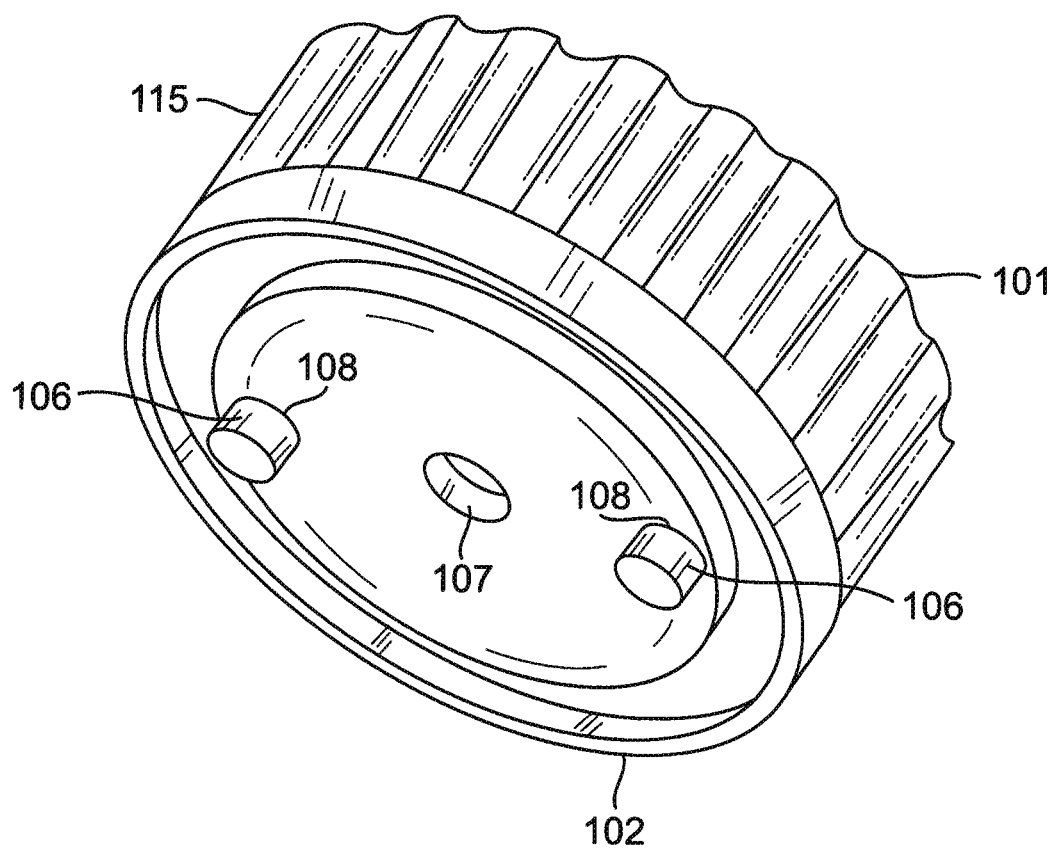
FIG. 28 is a perspective view of the tension control dial of FIG. 24 and locking plate of FIG. 25 as assembled.
Figure 29:
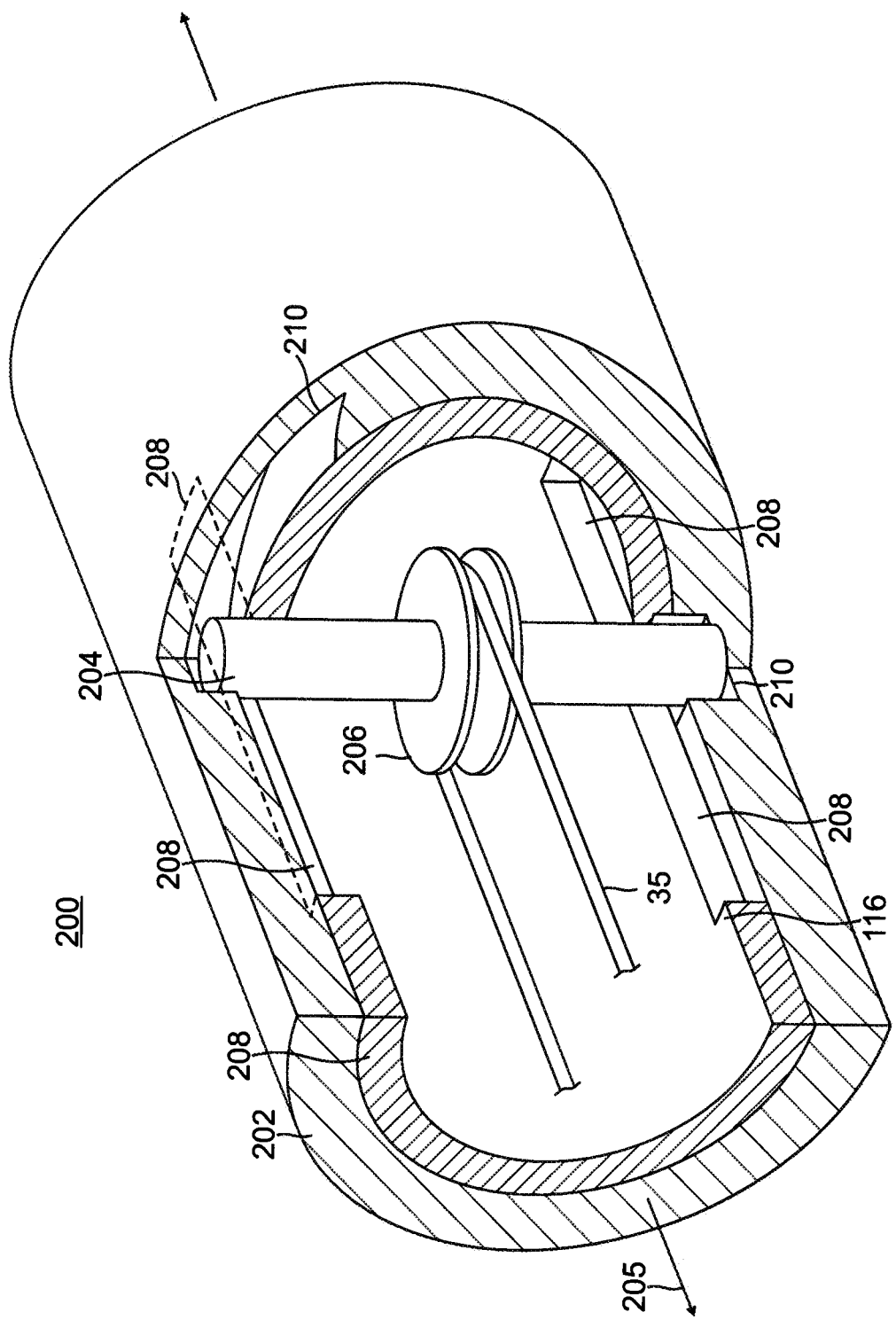
FIG. 29 is a perspective view of an embodiment of a rotational control assembly.
Figure 30:
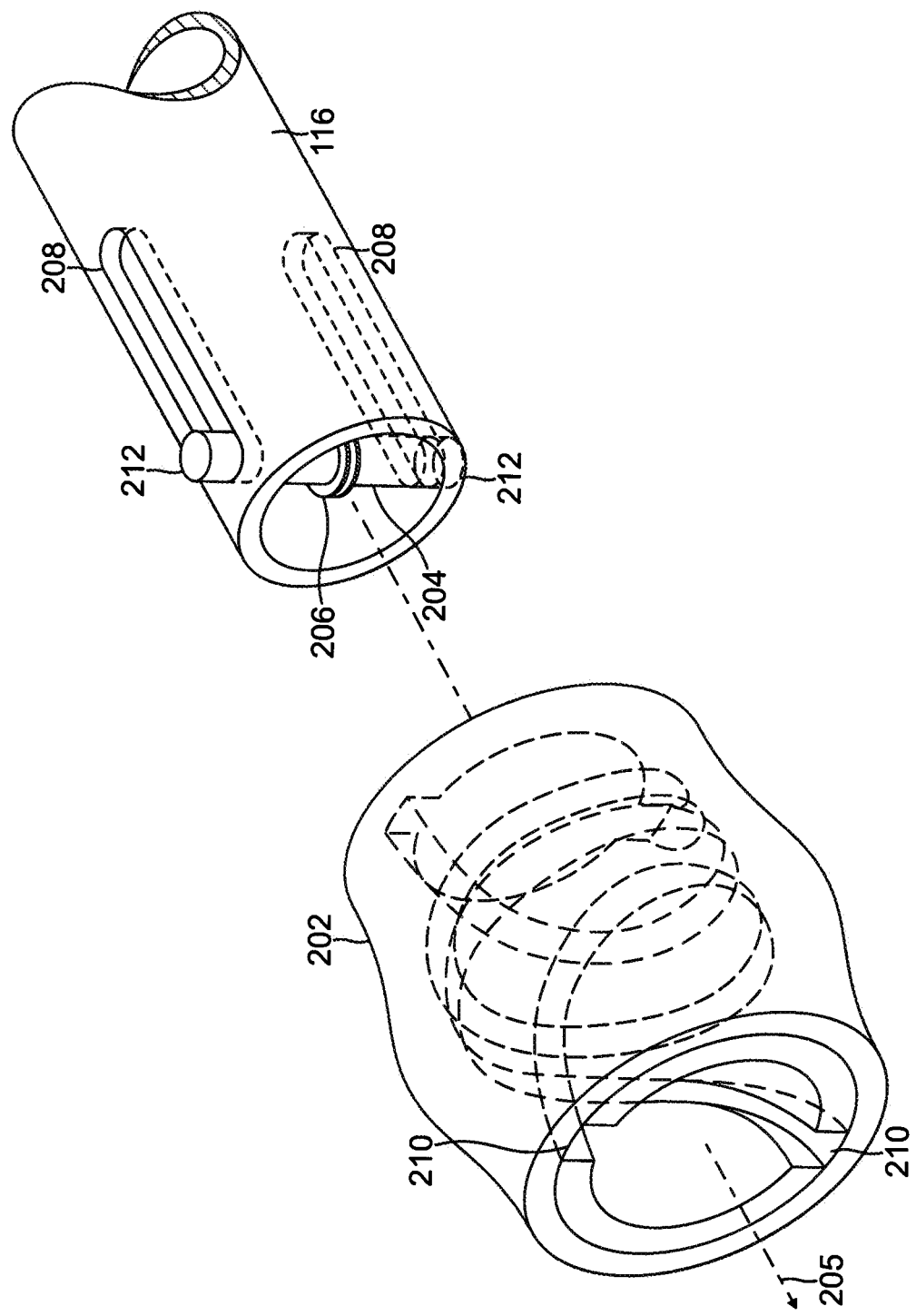
FIG. 30 is an exploded perspective view of the rotational control assembly of FIG. 29.

With reference to embodiment of FIGS. 1, 23 and 24, the rotational control assembly 200 is positioned proximal the deflection control assembly 74, although it is understood that it can be positioned distal the deflection control assembly 74. In the disclosed embodiment, the cam 202 is mounted on the proximal portion 116 of the control handle. The cam 202 can be formed from as a solid piece that slides onto the proximal portion and is snap-fitted over the two ends 212 of the shaft 204. Alternatively, the cam can be formed of two halves that are snap-fit to each other or joined by glue or sonic welding over the two ends of the shaft.

In operation, the rotational control assembly 200 is manipulated by means of the cam 202. As a user holds the control handle 16 and rotates the cam with his thumb and forefinger to contract or expand the mapping assembly, the two opposing helical tracks 210 on the inner surface are rotated relative to the proximal portion 116 thereby exerting a force on the shaft 204 via the ends 212 received in the tracks 210 to diametrically spin about the central longitudinal axis 205 of the control handle. However, because the shaft 204 extends through the guide slots 208 of the proximal portion 116, the guide slots limit the shaft to a translational movement proximally or distally along the longitudinal axis depending on the direction of rotation of the cam 202 as the ends 212 slide in the helical tracks 210. As the shaft 204 moves proximally or distally, the pulley 206 thereon correspondingly moves proximally or distally thereby drawing or releasing the third puller member 35. Advantageously, the rotational control assembly provides a multiplied linear motion of the third puller member, with greater sensitivity in the amount of motion controlled by the user. In the disclosed embodiment of FIG. 24, each helix 210 has a rotation of about 540° (360°±180°). However, it is understood that the rotation of each helix can range between about 180° to 720° depending on how much contraction/deflection and/or how much sensitivity is desired.

Lead wires and other components (e.g., thermocouple wires, cables, irrigation tubing) extending through proximal portion 116 in a protective tubing so as not to interfere with the interior components of the rotational control assembly.

In use, a suitable guiding sheath is inserted into the patient with its distal end positioned at a desired mapping location. An example of a suitable guiding sheath for use in connection with the present invention is the Preface™. Braiding Guiding Sheath, commercially available from Biosense Webster, Inc. (Irvine, Calif.). The distal end of the sheath is guided into one of the chamber, for example, the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the mapping assembly 17 returns to its original shape due to the shape-memory of the support member 54.

By manipulating and rotating the deflection arm 75 of the deflection control assembly 74 to deflect the intermediate section 14, the mapping assembly 17 is then inserted into a pulmonary vein or other tubular region (such as the superior vena cava, or inferior vena cava) so that the outer circumference of the generally circular main region 39 of the assembly 17 is in contact with a circumference inside the tubular region. Turning the deflection arm 75 in one direction deflects the intermediate section 14 to that direction. Turning the deflection 75 in the opposite direction deflects the intermediate section 14 to that opposite direction. Tension of the deflection 75 is adjusted by manipulating and rotating the dial 101. Turning the dial 101 in one direction increases the tension. Turning the dial 101 in the opposition direction decreases the tension. Preferably at least about 50%, more preferably at least about 70%, and still more preferably at least about 80% of the circumference of the generally circular main region is in contact with a circumference inside the tubular region.

The circular arrangement of the electrodes 26 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or the coronary sinus. By manipulating and rotating the cam 202 of the rotational assembly 200, the assembly 17, in particular, the generally circular main region 39, is contracted to fit the pulmonary vein or other tubular structure.

In accordance with a feature of the present invention, rotational motion of the cam results in linear motion of the shaft and the pulley along the central longitudinal axis of the control handle. The shaft rides along the helical grooves of the cam as it is rotated. The opposing linear guide slots of the proximal portion of the control handle ensure that the shaft maintains its general perpendicular orientation resulting in linear motion of the shaft relative to the proximal portion. As the shaft translates along the longitudinal axis, the pulley is also moved wherein its linear displacement results in twice the linear displacement of the third puller member. In the disclosed embodiment, the contraction wire is drawn proximally by the rotational control assembly to tighten and decrease the diameter of the generally circular region 39 when the cam is turned in one direction. By turning the cam in the opposition direction, the contraction wire 35 is released to release the generally circular region 39 such that it expands its diameter.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. It is understood that a feature of the present invention is applicable to multiplying linear motion of a puller wire, contraction wire, or any other object requiring insertion, removal, or tensioning within a medical device, including the disclosed electrophysiology catheter. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated body;
   a distal member distal of the elongated body, the distal member having a support member and a configuration;
   a control handle proximal of the elongated body;
   a magnetic-based sensor assembly including at least one conducting member comprising a wire having first and second ends, the wire comprising:
      a coil region that is wrapped around the support member; and
      a joint region adjacent the coil region, the joint region comprising:
         a first connection of the first end of the wire to a cable member at a first location proximal of the coil region, and
         a second connection of the second end of the wire to the cable member at a second location proximal of the coil region, wherein the second end of the wire extends through the coil region from a distal end of the coil region to the second location proximal of the coil region,
         a first strain relief construction comprising a first plurality of windings of the cable member around the support member proximal of the coil region, and
         a second strain relief construction comprising a second plurality of windings of the cable member around the support member proximal of the coil region, the second plurality of windings of the cable member being spaced from the first plurality of windings of the cable member;
      wherein the cable member is adapted to transmit a signal providing location information from the at least one conducting member to a mapping and localization system, and wherein the joint region provides strain relief to the coil region and the cable member from detaching.

2. The catheter of claim 1, wherein the first end of the wire forms a first amount of slack in the wire between the proximal end of the coil region and the first connection, and/or the second end of the wire forms a second amount of slack in the wire between the proximal end of the coil region and the second connection.

3. The catheter of claim 1, wherein the second plurality of windings of the cable member amounts to at least 720 degrees of winding around the support member.

4. The catheter of claim 1, wherein the magnetic-based sensor assembly further comprises a nonconductive tubing mounted on the support member, the coil region of the wire of the at least one conducting member being wrapped on the nonconductive tubing.

5. The catheter of claim 4, wherein the joint region is proximal of the nonconductive tubing.

6. The catheter of claim 1, wherein the first plurality of windings of the cable member amounts to at least 720 degrees of winding around the support member.

7. The catheter of claim 6, wherein the second plurality of windings of the cable member amounts to at least 720 degrees of winding around the support member.

8. The catheter of claim 1, wherein the joint region further comprises a third strain relief construction comprising a third plurality of windings of the cable member around the support member, the third plurality of windings of the cable member being spaced from both the first plurality of windings of the cable member and the second plurality of windings of the cable member.

9. The catheter of claim 8, wherein the windings of the third plurality of windings of the cable member are looser than the windings of the first plurality of windings of the cable member and the windings of the second plurality of windings of the cable member.

10. The catheter of claim 8, wherein the third plurality of windings of the cable member comprises diagonal windings.

11. The catheter of claim 1, wherein the magnetic-based sensor assembly further comprises a protective tubing over the coil region, joint region and first strain relief construction.

12. The catheter of claim 11, wherein the magnetic-based sensor assembly further comprises an epoxy or UV glue occupying a space inside of the protective tubing.

13. The catheter of claim 12, wherein the epoxy or UV glue forms end caps at each end of the protective tubing.

14. The catheter of claim 13, wherein one of the end caps covers the second strain relief construction.

15. The catheter of claim 1, wherein the at least one conducting member of the magnetic-based sensor assembly includes at least three conducting members, each of the at least three conducting members comprising a respective wire having respective first and second ends, each respective wire comprising:
 a respective coil region wrapped on the support member at a respective location along a length of the support member, and
 a respective joint region adjacent its respective coil region, the respective joint region comprising:
  a first respective connection of the first respective end of its respective wire to a respective cable member at a first respective location proximal of its respective coil region, and
  a second respective connection of the second respective end of its respective wire to the respective cable member at a second respective location proximal of its respective coil region,
  a first respective strain relief construction comprising a first respective plurality of windings of the respective cable member around the support member, and
  a second respective strain relief construction comprising a second respective plurality of windings of the respective cable member around the support member, the second respective plurality of windings of the respective cable member being spaced from the first respective plurality of windings of the respective cable member;
 each respective cable member being adapted to transmit a respective signal providing location information from its respective conducting member to the mapping and localization system, and each respective joint region provides strain relief to its respective coil region and its respective cable member from detaching.

16. The catheter of claim 15, wherein the second respective end of its respective wire extends through its respective coil region from a distal end of its respective coil region to the second respective location proximal of its respective coil region.

17. The catheter of claim 15, wherein the first respective end of its respective wire forms a first respective amount of slack in its respective wire between the proximal end of its respective coil region and its first respective connection, and/or the second end of its respective wire forms a second respective amount of slack in its respective wire between the proximal end of its respective coil region and its second respective connection.

18. The catheter of claim 15, wherein each respective joint region further comprises a third respective strain relief construction comprising a third respective plurality of windings of the respective cable member around the support member, the third respective plurality of windings of the respective cable member being spaced from both the first respective plurality of windings of the respective cable member and the second respective plurality of windings of the respective cable member.

19. The catheter of claim 18, wherein the windings of the third respective plurality of windings of the respective cable member are looser than the windings of the first respective plurality of windings of the respective cable member and the windings of the second respective plurality of windings of the respective cable member.

\* \* \* \* \*